US011986304B2

(12) United States Patent
Manoli et al.

(10) Patent No.: US 11,986,304 B2
(45) Date of Patent: May 21, 2024

(54) SENSOR ARRAYS, METHOD FOR OPERATING A SENSOR ARRAY AND A COMPUTER PROGRAM FOR PERFORMING A METHOD FOR OPERATING A SENSOR ARRAY

(71) Applicant: Albert-Ludwigs-Universität Freiburg, Freiburg (DE)

(72) Inventors: Yiannos Manoli, Freiburg (DE); Daniel De Dorigo, Freiburg (DE); Christian Moranz, Buchenbach (DE); Hagen Graf, Oslo (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 959 days.

(21) Appl. No.: 16/986,322

(22) Filed: Aug. 6, 2020

(65) Prior Publication Data

US 2020/0359921 A1 Nov. 19, 2020

Related U.S. Application Data

(63) Continuation of application No. PCT/EP2019/053140, filed on Feb. 8, 2019.

(30) Foreign Application Priority Data

Feb. 9, 2018 (DE) ...................... 10 2018 202 073.6

(51) Int. Cl.
*A61B 5/293* (2021.01)
*A61B 5/00* (2006.01)
*A61B 5/24* (2021.01)

(52) U.S. Cl.
CPC ................ *A61B 5/24* (2021.01); *A61B 5/293* (2021.01); *A61B 5/6848* (2013.01); *A61B 2562/043* (2013.01)

(58) Field of Classification Search
CPC ........ A61B 2562/164; A61B 2562/166; A61B 5/302; A61B 5/31; A61B 5/25;
(Continued)

(56) References Cited

U.S. PATENT DOCUMENTS

| 2013/0041235 A1* | 2/2013 | Rogers ................. H05K 1/0283 |
| | | 600/386 |
| 2014/0194944 A1* | 7/2014 | Romanelli ............. A61B 5/369 |
| | | 607/45 |

(Continued)

FOREIGN PATENT DOCUMENTS

| CN | 103648367 A | 3/2014 |
| JP | 2014-514944 A | 6/2014 |

OTHER PUBLICATIONS

Japanese language office action dated Nov. 24, 2021, issued in application No. JP 2020-565537.
(Continued)

*Primary Examiner* — Eun Hwa Kim
(74) *Attorney, Agent, or Firm* — McClure, Qualey & Rodack, LLP

(57) ABSTRACT

A sensor array includes a base for providing a probe signal and a plurality of modular recording sites. Each modular recording site of the plurality of modular recording sites is configured for receiving a signal, for converting the signal into a digital sensor signal and to provide the digital sensor signal to the base. The base is configured for receiving a plurality of digital sensor signals from the plurality of modular recording sites and to process the plurality of digital sensor signals so as to provide the probe signal.

22 Claims, 15 Drawing Sheets

(58) Field of Classification Search
CPC ..... A61B 5/293; A61B 5/6846; A61B 5/6847; A61B 5/6868
See application file for complete search history.

(56) References Cited

U.S. PATENT DOCUMENTS

| | | | |
|---|---|---|---|
| 2014/0303452 A1* | 10/2014 | Ghaffari | H01L 27/14687 601/3 |
| 2015/0313501 A1 | 11/2015 | Shachar | |
| 2018/0078194 A1* | 3/2018 | Han | A61B 5/6868 |

OTHER PUBLICATIONS

English language translation of office action dated Nov. 24, 2021, issued in application No. JP 2020-565537.

Chinese language office action dated Apr. 6, 2023, issued in application No. CN 201980023270.5.

English language translation of office action dated Apr. 6, 2023, issued in application No. CN 201980023270.5 (pp. 1-8 of attachment).

G. Buzsaki et al.: "Tools for Probing Local Circuits: High-Density Silicon Probes Combined with Optogenetics," Neuron, vol. 86, pp. 92-105, 2015.

K. Seidl et al.: "CMOS-Based High-Density Silicon Microprobe Arrays for Electronic Depth Control in Intracortical Neural Recording-Characterization and Application," in Journal of Microelectromechanical Systems, vol. 21, No. 6, pp. 1426-1435, Dec. 2012.

A. S. Herbawi et al.: "High-density CMOS neural probe implementing a hierarchical addressing scheme for 1600 recording sites and 32 output channels," Transducers, pp. 20-23, 2017.

V. Viswam et al.: "High-density mapping of brain slices using a large multi-functional high-density CMOS microelectrode array system," Transducers, pp. 135-138. 2017, doi: 10.1109/TRANSDUCERS.2017.7994006.

B.C. Raducanu et al.: "Time multiplexed active neural probe with 678 parallel recording sites", IEEE ESSDERC, 2016, pp. 385-388.

C.M. Lopez et al.: "22.7 A 966-electrode neural probe with 384 configurable channels in 0.13μm SOI CMOS," ISSCC Dig. Tech. Papers, pp. 392-393, 2016.

F Heer et al.: "CMOS microelectrode array for the monitoring of electrogenic cells", Biosensors and Bioelectronics, vol. 20, pp. 358-366, 2004, ISSN 0956-5663, doi: 10.1016/j.bios.2004.02.006.

J. Scholvin et al.: "Close-packed silicon microelectrodes for scalable spatially oversampled neural recording", IEEE Trans. Biomed. Eng., vol. 63, pp. 120-130, 2016.

T.D.Y. Kozai et al.: "Photoelectric Artefact from Optogenetics and Imaging on Microelectrodes and Bioelectronics: New Challenges and Opportunities," J. Mater. Chem. B, pp. 4965-4978, 2015.

L. Zhang et al.: „ A 15-bit Two-Step Pixel-Level ADC for 17μm-Pitch Low-Power and High-Dynamic-Range IRFPA; 2015, Published in: 2015 IEEE International Symposium on Circuits and Systems (ISCAS); pp. 670-673.

S. Yang et al.: A 16-bit two-step pixel-level ADC for 384*288 Infrared Focal Plane Array; 2017; Published in: 2017 IEEE 12th International Conference on ASIC (ASICON); pp. 780-783.

D. X. D. Yang et al.: A 640 × 512 CMOS Image Sensor with Ultrawide Dynamic Range Floating-Point Pixel-Level ADC; 1999; IEEE Journal of Solid-State Circuits, vol. 34, No. 12, Dec. 1999; pp. 1821-1834.

Z. Ignjatovic et al.: "A 0.88nW/pixel, 99.6 dB Linear-Dynamic-Range Fully-Digital Image Sensor Employing a Pixel-Level Sigma-Delta ADC"; Published in: 2006 Symposium on VLSI Circuits, 2006. Digest of Technical Papers.

C. H. Hwang et al.: "Readout integrated circuits involving pixel-level ADC for microbolometers"; 2008 International SoC Design Conference; pp. III-70-III-71.

Z. Huang et al.: "A 16-bit Single-Slope based Pixel-level ADC for 15μm-pitch 640×512 MWIR FPAs"; 2018; Published in: 2018 IEEE International Symposium on Circuits and Systems (ISCAS).

J. P. Crooks et al.: "A CMOS Image Sensor With In-Pixel ADC, Timestamp, and Sparse Readout"; IEEE Sensors Journal, vol. 9, No. 1, Jan. 2009; pp. 20-28.

Written opinion, in PCT/EP2019/053140, dated Jun. 3, 2019.

International Search Report, in PCT/EP2019/053140, dated Jun. 3, 2019.

D. X. D. Yang et al.: "A Nyquist-Rate Pixel-Level ADC for CMOS Image Sensors"; 1999; IEEE Journal of Solid-State Circuits, vol. 34, No. 3, Mar. 1999; pp. 348-356.

* cited by examiner

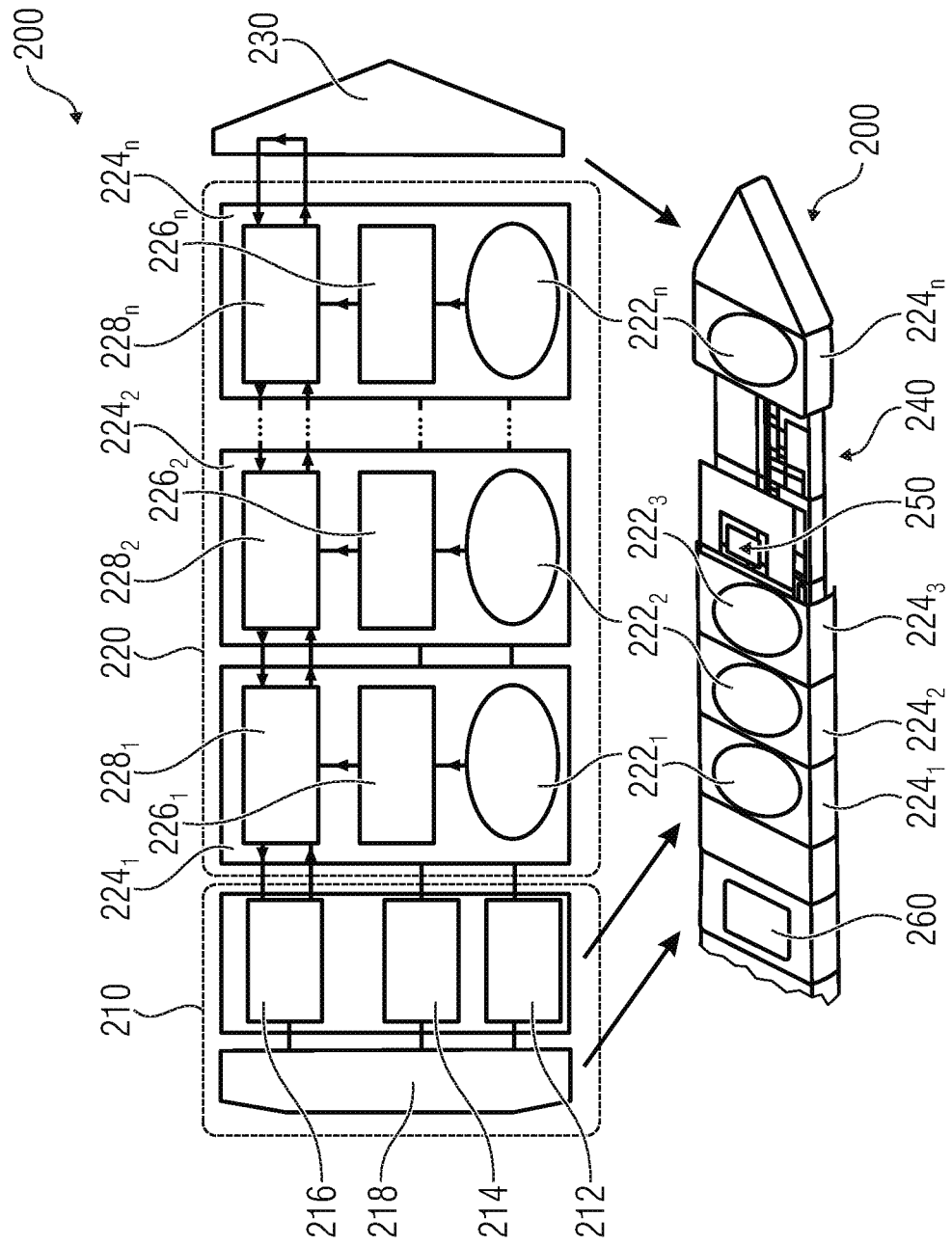

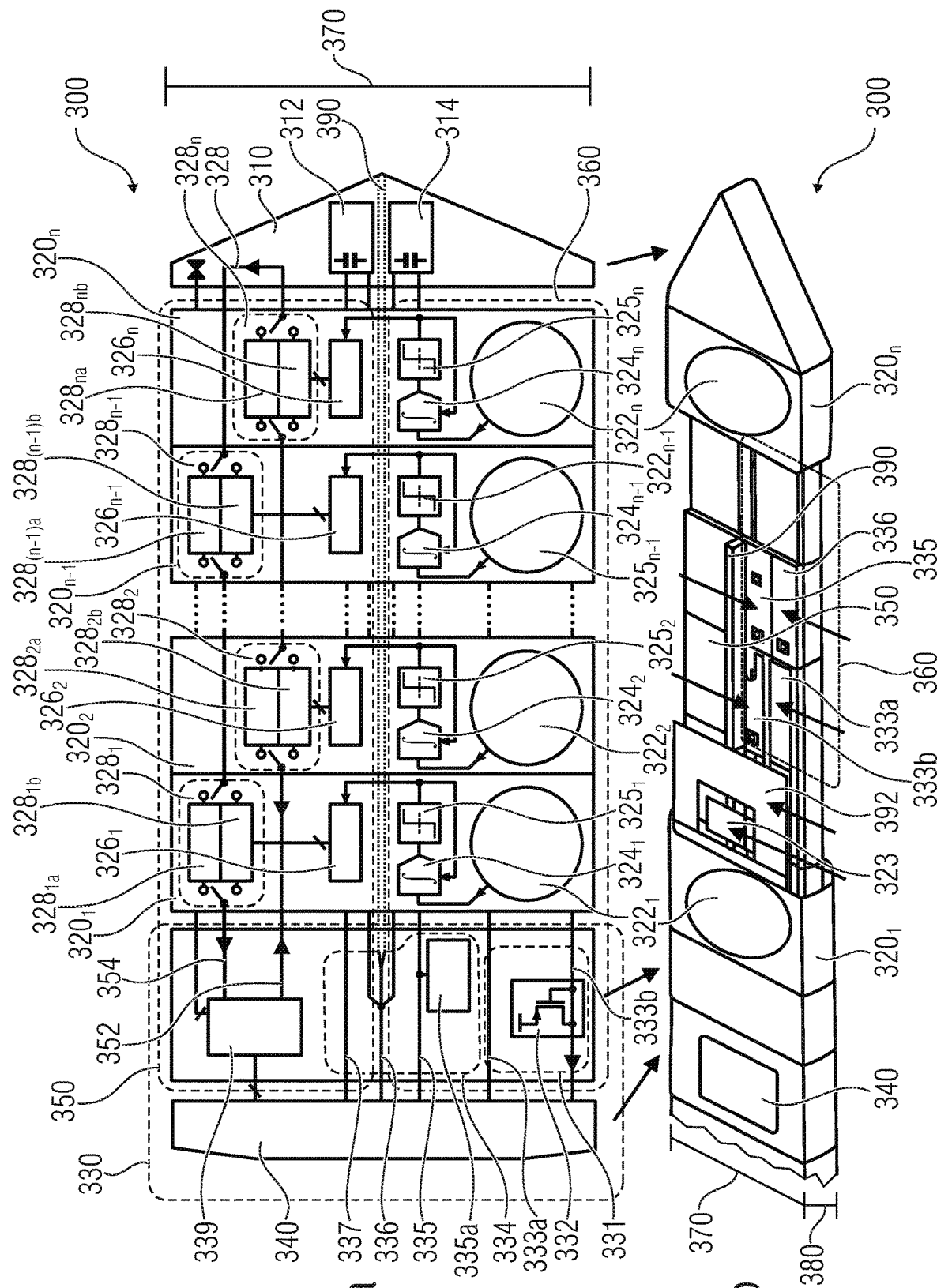

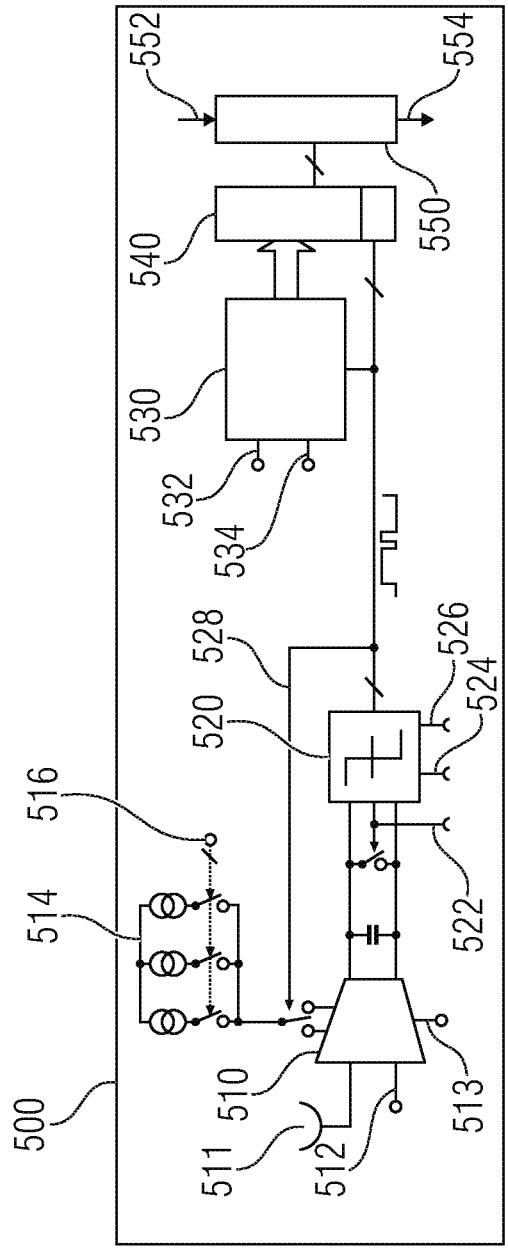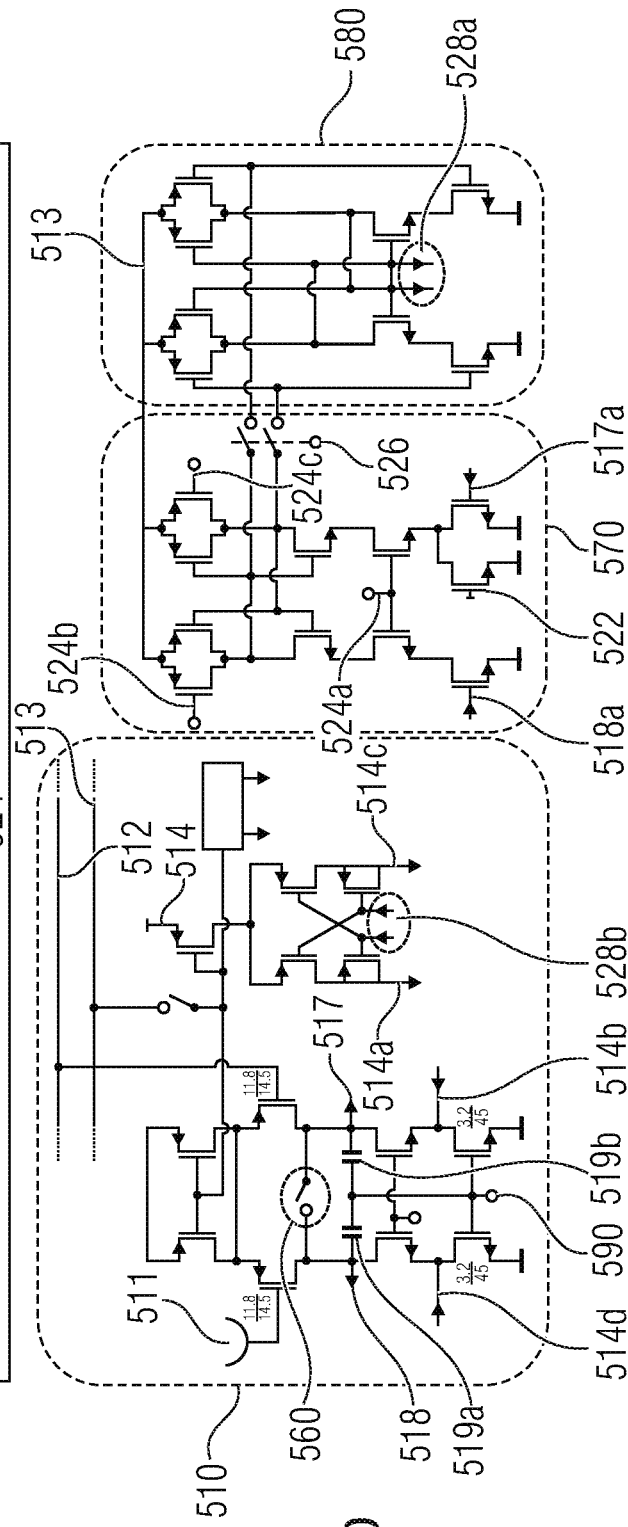
Fig. 5a
Fig. 5b

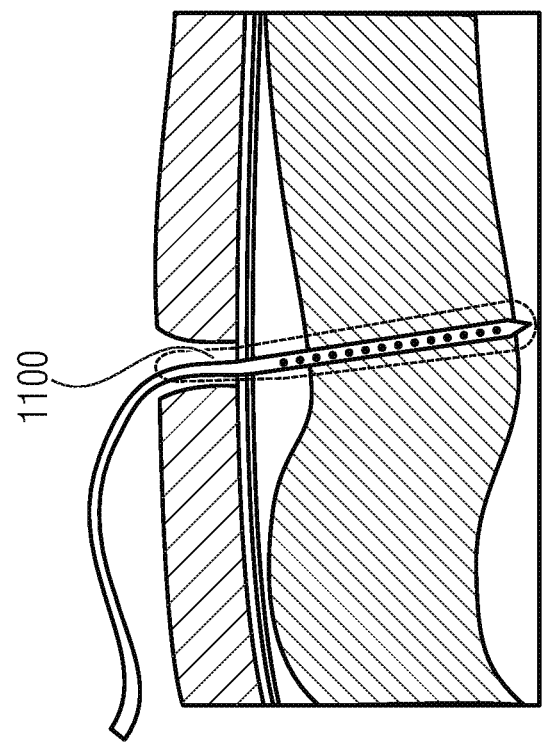
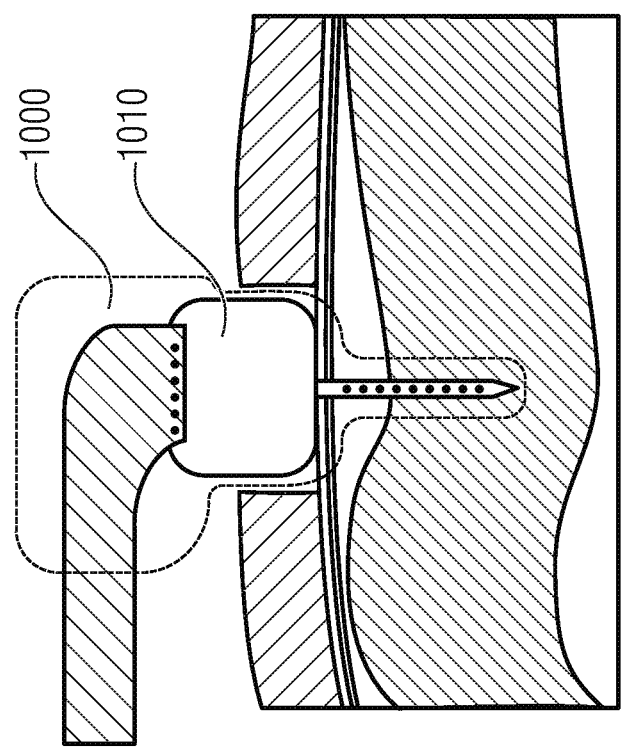

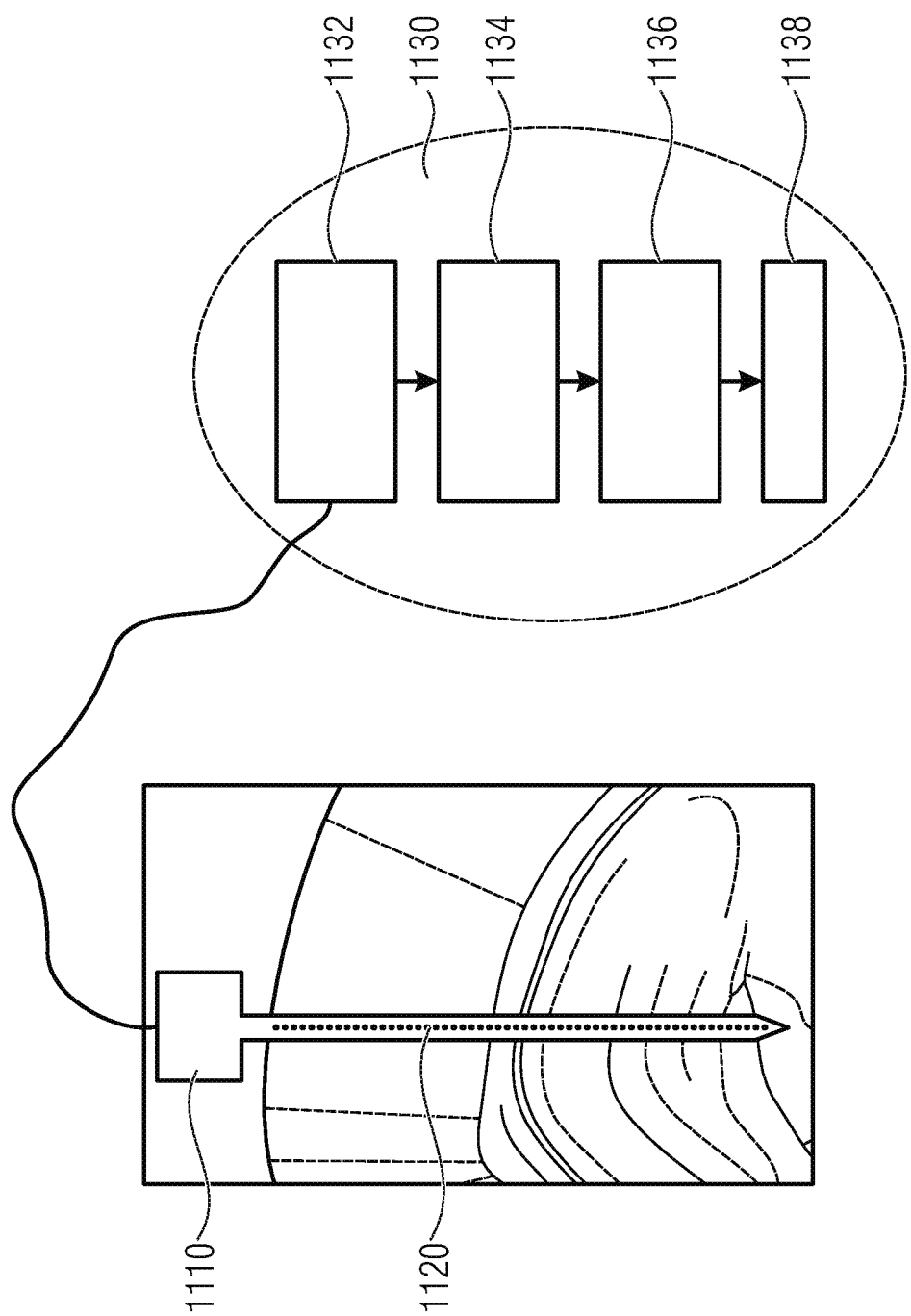

SENSOR ARRAYS, METHOD FOR OPERATING A SENSOR ARRAY AND A COMPUTER PROGRAM FOR PERFORMING A METHOD FOR OPERATING A SENSOR ARRAY

CROSS-REFERENCE TO RELATED APPLICATIONS

This application is a continuation of copending International Application No. PCT/EP2019/053140, filed Feb. 8, 2019, which is incorporated herein by reference in its entirety, and additionally claims priority from German Application No. 10 2018 202 073.6, filed Feb. 9, 2018, which is also incorporated herein by reference in its entirety.

Embodiments according to the invention relate to sensor arrays such as neuronal probes, a method for operating a sensor array and a computer program for performing a method for operating a sensor array.

BACKGROUND OF THE INVENTION

In sensor applications, such as a in biomedical measurement technology, frequently, a large number (more than 100) of sensor signals in the body have to be contacted and carried to external electronics. This is in particular the case for neuronal sensors where a number of small sensors and electrodes, respectively, which is as large as possible, are attached to a device for detecting neuronal signals in the brain tissue. The signals are carried to the outside to a computer control system which can process and store the signals. Such neuronal sensor systems are applied in neuroscience or generally in fields of application dealing with brain activity research.

Typically, neuronal needles consist of a plurality of electrodes and electric conductive traces carrying the signals to a base at the top-end of the needle. At this end a cable is attached to carry the signals to an external signal processing device. Typically, signal processing consists of a chain of preamplifier, filter and analog-digital converter. While in passive needles no active readout electronics is implemented in the needle, the electronics are partly or completely integrated in the base in active needles.

Neuronal signals can be divided into two main types, low frequency signals (local field potentials) with amplitudes of up to several millivolts and high frequency signals (action potentials) with amplitudes up to several hundred millivolts.

Since the amplitudes are very small, the same are also susceptible to interference sources, in particular when the conductor carrying the signal to the outside has a length of several centimeters.

By parasitic effects, such as line capacitances, different signals can interfere with each other on one needle, such that original source/electrode can no longer be identified (crosstalk).

The requirement that the neuronal needles, typically have to be introduced into the brain tissue results in another important aspect for the application: tissue damages during surgical introduction into the brain tissue are to be minimized. For that reason, needles need to have a cross-sectional area that is as small as possible. While this has been successfully realized so far for the shaft, all neuronal needles published so far have a large base which cannot be embedded into the brain tissue due to its size. Thus, the maximum introduction depth is limited to the length of the needle.

Another procedure to evaluate the neuronal signals is the usage of multi-electrode-arrays (MEA). In such systems brain slices can be placed on a two-dimensional array of neuronal sensors and the neuronal activity of the brain slices can be measured.

Generally, a great number of neuronal probes of different designs that can be used for the described applications exist already. All known systems can be classified based on the degree of electronic integration.

Neuronal evaluation systems can be divided into three groups.

One group comprises passive systems without electronics. Such systems consist of electrodes and electrical conductors, wherein the conductors guide the signals from a sensor to an external interface. There exists a plurality of different implementations, mostly on flexible substrates. An overview can be found in [1]. These systems are restricted to a small number of electrodes.

Another group comprises passive electronic systems. In passive CMOS sensor systems, no active evaluation electronics is implemented, but merely electronically-controlled switching allowing a connection of a specific sensor element (for example an electrode) with one of the conductors that lead to the output contacts. The evaluation electronics is located outside the system. The number of electrodes that can be readout simultaneously is limited by the number of contacts on the base. The papers [2] and [3] describe neuronal needles, whereas paper [4] introduces a two-dimensional MEA-system, which is based on the passive concept.

The third group comprises active electronic systems. In active needles, part of the evaluation electronics is integrated in the chip [5, 6]. Here, the signal chain (for example signal amplifier, analog-to-digital conversion, digital processing/interface) is integrated in the base. Similar to [2] and [3], the shaft itself includes electronically-controlled switches and preamplifiers that carry the neuronal signals from selected electrodes to the base. A similar active MEA-System is however described in [7]. Additionally to switches for the selection of a sensor node, a part of the evaluation circuit is integrated in the sensor array (filter and preamplifier). The conversion from analog to digital is outside of the sensible area.

The known solutions show disadvantage. All known solutions have a very large base (electronics outside of the sensible area) and hence cannot, in case of neuronal needles, completely be immersed in the tissue. Additionally, the size of the base involves an invasive surgical procedure. The number of sensor nodes (for example electrodes) that can be readout in parallel depends on the shaft width and the available area, respectively, for carrying analog signals from the electrodes to the base electronics. For carrying the signals to the outside, other solutions have many terminals and are hence difficult to handle. In passive needles, the number of terminals is directly proportional to the number of electrodes that can be read out simultaneously.

Known solutions carry sensitive neuronal signals from the sensors to the base. Thus, the same are particularly sensitive against external interference sources, as well as susceptible to crosstalk between the channels, in comparison to passive systems active concepts improve the signal integrity by pre-amplifying the signals on-site (in-situ/under the electrode). All known concepts are not suitable for reading out an arbitrary number of electrodes simultaneously. Furthermore, the conductors in the shaft still guide analog signals, which are in fact amplified, but not completely insensitive to disturbances.

As the number of electrodes increases, conventional devices need either a large number of interconnects at the base of the probe or allow only a reduced number of electrodes to be read out simultaneously [8, 3].

Therefore, it is desired to get a concept which makes a better compromise between reducing the size of the base, enabling a simultaneous readout of an arbitrary number of sensor nodes and complexity.

SUMMARY

According to an embodiment, a sensor array may have: a base for providing a probe signal; a plurality of modular recording sites, wherein each modular recording site of the plurality of modular recording sites includes a CMOS silicon substrate, at least one sensor element configured for receiving an analog biosignal, an in-situ analog-to-digital converter configured for converting the analog biosignal into a digital sensor signal and a communication interface configured to provide the digital sensor signal to the base; wherein the communication interfaces of the plurality of modular recording sites are connected serially with respect to each other and to the base.

According to another embodiment, a method for operating an inventive sensor array may have the following steps: recording of an analog biosignal with a sensor of a modular recording site of a plurality of modular recording sites of the sensor array; converting of the analog biosignal into a plurality of digital sensor signals using the plurality of modular recording sites of the sensor array; providing of the plurality of digital sensor signals to a base of the sensor array using communication interfaces of the plurality of modular recording sites of the sensor array; providing the digital sensor signal to the base using a communication interface of the modular recording site, serially by using the communication interfaces of the plurality of modular recording sites being connected serially with respect to each other and to the base; receiving of the plurality of digital sensor signals from the plurality of modular recording sites of the sensor array with the base of the sensor array; processing of the plurality of digital sensor signals by the base of the sensor array so as to obtain a probe signal; and providing the probe signal with the base of the sensor array for a remote device.

Another embodiment may have a non-transitory digital storage medium having a computer program stored thereon to perform the inventive method for operating an inventive sensor array when said computer program is run by a computer.

A finding of the present invention is that by converting an analog signal to be measured, in particular a biosignal such as biomedical signals, e.g., biochemical signals and more specific a neuronal signal as being obtainable from neurons, muscles, brains or other parts of the body such as ears and/or eyes, into a digital sensor signal locally, i.e., at the place of the electrode, a digital sensor signal may be obtained. Thus it is more efficient and reduces the complexity when the received biosignal by each modular recording site of the plurality of modular recording sites is converted directly in each modular recording site into a digital sensor signal before providing the digital sensor signal to the base. Thus, the signal chain (as stated in the art) of the readout electronics is reduced by omitting preamplification, amplification and filtering and is replaced by direct local analog-to-digital conversion of the biosignals (for example sensor signals). Since only digital sensor signals (respectively, digital data) and no sensitive signals (for example analog signals) are carried from each modular recording site of the plurality of modular recording sites to the base (for example along a shaft), (nearly) no crosstalk can be measured between each modular recording site (for example sensors) and there is high robustness with respect to external interference sources, such as light sources or electromagnetic fields. Thus the digital sensor signal is robust against distortions and/or may be combined with a plurality of further signals allowing for small communication interfaces. Further, a small base is obtained despite the possible high number of recording sites carrying sensor elements for the measurement.

Sensor arrays such as neuronal probes, according to embodiments may be implemented with a small size of the base by maintaining a high efficiency, whereby the complexity can be low by a conversion of the biosignal into a digital signal locally at each modular recording site of the plurality of modular recording sites. This conversion allows for contacting a high or even an arbitrary number of modular recording sites.

An embodiment according to this invention is related to a sensor array comprising a base configured for providing a probe signal. The sensor array also comprises a plurality of modular recording sites. Each modular recording site of the plurality of modular recording sites is configured for receiving a signal, for converting the signal into a digital sensor signal and to provide the digital sensor signal to the base. The base is configured for receiving a plurality of digital sensor signals from the plurality of modular recording sites and to process the plurality of digital sensor signals so as to provide the probe signal.

Each modular recording site of the plurality of modular recording sites receives, for example, a biosignal representing the signal. In other words, the signal is according to an embodiment a biosignal. The biosignal is an analog signal so that the conversion from the biosignal to a digital sensor signal is performed by an analog-to-digital conversion. This is, for example, realized by an analog to digital converter implemented in each modular recording site. The digital sensor signal from each modular recording site of the plurality of modular recording is, for example, received by the base. Thereby, it is, for example, not needed that the base comprises an analog-to-digital converter like active sensor arrays stated in the art. Thus, the base is, for example, implemented with a small size, because the base needs few components like, for example, conductors respectively, for all recording sites and/or ADCs (analog-to-digital converter), and/or filter and/or amplifier compared to the base of a sensor array stated in the art. The direct conversion of the biosignal into a digital sensor signal by each modular recording site of the plurality of modular recording sites makes it possible to contact an arbitrary number of modular recording sites of the plurality of modular recording sites.

In an embodiment, each modular recording site of the plurality of modular recording sites comprises a communication interface. The communication interface can, for example, receive configuration data from the base. Based on the received configuration data, the modular recording site can, for example, adapt parameters relating to the operation of the modular recording site. The configuration data can, for example, hold information about the state of each modular recording site, for example an on-state or an off-state of the modular recording site. Thus, it can be chosen which modular recording site should record and therefore receive a signal. Information which, for example, can be received in the form of configuration data may include a change of the scaling of the conversion from analog to digital. The communication interface is an interface enabling communication between each modular recording site and the base. In this case the communication interface, for example, operates in a configuration mode.

In an embodiment of the sensor array, each modular recording site of the plurality of modular recording sites is configured for providing the digital sensor signal to the base using a communication interface of each modular recording site. The communication interfaces of the plurality of modular recording sites are connected serially with respect to each other and to the base. This can mean that all modular recording sites of the plurality of modular recording sites can be read out simultaneously. In this case the communication interface is, for example, in a normal operating mode. Each communication interface of each modular recording site, for example, transfers the respective digital sensor signal of each modular recording site in sequence respective to a position of each modular recording site with respect to a position of each other modular recording site. In that way, the digital sensor signals of each modular recording site can be linked to the digital sensor signals of the neighboring modular recording sites and can be carried to the base, in that way, for example, the number of connections from one modular recording site of the plurality of modular recording sites to a neighboring modular recording site of the plurality of modular recording sites is kept very small and no analog signal (for example the received biosignal by each modular recording site) susceptible to interferences is carried to the base. Since all signals are digitized (this means, for example, that each biosignal received by a modular recording site of the plurality of modular recording sites is converted into a digital sensor signal) directly on-site (for example on each modular recording site), and send serially by a communication interface to the base, the sensor array needs only a very small number of lines to the base. Thus, the sensor array not only reduces the complexity but also the size of the base and shaft of the sensor array, because only a reduced number of lines from each modular recording site of the plurality of modular recording sites is needed to transfer a digital sensor signal to the base. The serial connection of the communication interfaces of the plurality of modular recording sites with respect to each other and to the base also enables the sensor array to contact an arbitrary number of modular recording sites.

Thus, this modular system concept allows, for example, the contacting of an arbitrary number of modular recording sites (for example neuronal electrodes of any topology or geometry) with minimum complexity, a small size of the base and reading out the modular recording sites simultaneously.

In an embodiment, each modular recording site of the plurality of modular recording sites comprises a communication interface. The communication interface comprises a serial interface. The communication interfaces of the plurality of modular recording sites are, for example, connected to each other in a serial communication chain comprising a forward path from the base to a sensor array endpoint of the sensor array and a backward path from the sensor array endpoint to the base. Wherein the sensor array endpoint is a biomedical sensor array endpoint, in particular a tip.

For each pair comprising a first modular recording site and a directly adjacent neighboring second modular recording site, the communication interface of the first modular recording site is connected to the forward path and the communication interface of the second modular recording site is connected to the backward path. The digital sensor signals from each modular recording site as well as a clock are, for example, forwarded from one modular recording site to a next modular recording site (for example, to a directly adjacent neighboring modular recording site). The clock is, for example, slightly delayed from each modular recording site to each modular recording site to spread digital supply noise and reduce peak current consumption.

The modular recording sites are, for example, grouped into blocks of two modular recording sites comprising a first modular recording site connected to the forward chain and forward clock and a second modular recording site connected to the backward chain and backward clock. Thus, for example, the serial interfaces of every second modular recording site are connected/coupled to a forward chain and the serial interfaces of all other modular recording sites are connected/coupled to a backward chain. The first chain and the second chain are coupled to the base such that the digital sensor signal is transferred to the base. Alternatively, instead of using pairs of modular recording sites for the forward and backward chain also multiples of two (for example, 4 modular recording sites, the first two connected to the forward chain and the second two connected to the backward chain, or 6 modular recording sites, the first three connected to the forward chain and the second three connected to the backward chain) may be used or even only single modules with only one chain in one direction. In the latter case of only one chain, an additional digital wire from the end of the chain to the base may serve as backward path, when all modular recording sites are connected to the forward chain or an additional digital wire from the base to the end of the chain is to serve as forward path, when all modular recording sites are connected to the backward chain. An implementation using pairs of modular recording sites on the forward path and the backward path is more efficient compared to a single module solution, where only one path either the forward path or the backward path is used but not mandatory. Thus each digital sensor signal provided by each modular recording site can be transferred very fast to the base and according to an embodiment only digital signals are exchanged between each modular recording site and the base. It is possible to read out the plurality of modular recording sites simultaneously and each digital sensor signal transferred to the base can be assigned to a specific modular recording site, because of the implementation of a forward chain and a backward chain connecting each modular recording site with each modular recording site and the base.

In an embodiment, the base is configured to receive a combined sensor signal from the plurality of modular recording sites, the combined sensor signal comprising the digital sensor signals of each of the modular recording sites. The combined sensor signal is, for example, a sequence of each digital sensor signal of each modular recording site, or a superposition of each digital sensor signal of each modular recording site with each digital sensor signal of each modular recording site. This implementation can, for example, reduce the complexity of the sensor array and reduce the size of the base, because there is only one digital data bus needed which connects each modular recording site of the plurality of modular recording sites with the base and transfers a combined digital sensor signal to the base.

In an embodiment accordingly each modular recording site of the plurality of modular recording sites comprises a communication interface. The communication interfaces of the plurality of modular recording sites are connected in parallel with respect to each other and to the base. This can, for example, be understood as a parallel interface between the plurality of modular recording sites and the base. This means, for example, that all digital sensor signals from the plurality of modular recording sites are sent to the base in parallel. For example, several chains can be implemented and read out in parallel, such as a first chain, wherein a first modular recording site and a second modular recording site are connected to the first chain, a second chain, wherein a third modular recording site and a fourth modular recording site are connected to the second chain, a third chain, wherein a fifth modular recording site and a sixth modular recording site are connected to the third chain and a fourth chain, wherein a seventh modular recording site and an eighth modular recording site are connected to the first chain. This means, for example, that four chains are couplet to the base, wherein the base is configured to read out the four chains simultaneously and serialize the incoming digital sensor signals for an external interface. This embodiment has the advantage, that data in form of digital sensor signals can be read out very fast and thus the sensor array gets more efficient.

In an embodiment, each modular recording site of the plurality of modular recording sites comprises a delta-sigma analog digital converter. Since even the largest biosignals, in particular neuronal signals are only in the range of some tens of millivolts and the needed linearity is low, a direct conversion (for example by each modular recording site) using a Gm-C (integrator using a transconductance Gm of an amplifier in combination with a capacitance C) based incremental delta-sigma-analog-digital-converter in each modular recording site is implemented. The first-order modulator (for example the delta-sigma-ADC (ADC is an analog-digital converter)) allows the implementation on a minimal silicon area, since only one integrator and capacitor and no accurate time constants, thus no local biasing, are needed. The usage of a delta-sigma analog digital converter by each modular recording site of the plurality of modular recording sites has the advantage that the received signal by each modular recording site can be converted into a digital sensor signal directly at each modular recording site. Thus, from each modular recording site to the base (nearly) insensitive digital sensor signals to electromagnetic interferences or crosstalk are sent. Thereby, the sensor array gets very accurate. Another advantage of this embodiment is that the signals transferred from each modular recording site of the plurality of modular recording sites to the base are already digitized instead of sensor arrays as in conventional technology, where the conversion of the signals to a digital sensor signal is implemented in the base, which makes the base very big, but with the sensor array according to this invention the size of the base can be small. The continuous-time delta-sigma converter is known for their reduced current demand. Furthermore, the delta-sigma-analog-digital converter is known for comprising an implicit antialiasing filter effect. Thus, more current and additional area can be saved, because the necessity for a dedicated antialiasing filter as an additional circuit block can be omitted. Thus, the complexity of the sensor array is low.

In an embodiment, each modular recording site of the plurality of modular recording sites comprises an integrator and a quantizer configured to convert directly the signal into a digital sensor signal. The integrator is, for example, an OTA-C integrator (respectively, operational trans-conductance amplifier plus capacitance), i.e. a single stage delta-sigma ADC. But it is also feasible to implement even higher order ADCs (higher order means more integrators), which may be more optimal for different designs of the sensor array. The output of the single branch OTA-C integrator is connected to the quantizer, i.e., comparator and output latch, driving the switches for a current feedback. The integrator of each modular recording site of the plurality of modular recording sites is configured to receive the signal and to integrate the signal, so as to obtain an integrated signal. The quantizer of each modular recording site of the plurality of modular recording sites comprises a latched comparator end an output latch. The latched comparator is configured to receive the integrated signal and to quantize the integrated signal. The output latch is configured to drive feedback switches for a current feedback to the integrator, based on the comparator output. The noise of the feedback current and the feedback switches, which operate at digital level input signals, is negligible compared to the major noise contributors. An implementation with a Gm-C integrator has, for example, additionally the advantage that the area in demand is very small. Another advantage of the usage of an integrator and a quantizer directly by each modular recording site is that no preamplifier is needed. With the integrator and the quantizer the signal can directly be converted into the digital sensor signal by each modular recording site. Thus, digital sensor signals are transferred from each modular recording site of the plurality of modular recording sites to the base. In sensor arrays, as in conventional technology, the biosignal is transferred as an analog signal to the base and therefore a preamplifier is needed.

In an embodiment, each modular recording site of the plurality of modular recording sites is configured for converting the signal into the digital sensor signal independently of neighboring modular recording sites. This has the advantage that the signal received by each modular recording site of the plurality of modular recording sites does not have to be transferred as an analog signal, for example to the next modular recording site or directly to the base, but instead is converted directly by each modular recording site into a digital sensor signal. Thus, the sensor array is nearly insensitive to electromagnetic interferences or crosstalk.

In an embodiment, one modular recording site of the plurality of modular recording sites comprises at least one sensor element configured for detecting the signal. The sensor element may be an electrode, an optical sensor and/or a chemical sensor. It is also, for example, possible to have one modular recording site with, for example, three sensor elements. This means, for example, that more than one sensor element shares an electronic circuitry in one modular recording site of the plurality of modular recording sites for converting the analog signal into a digital sensor signal. Thus, the number of components is reduced and therefore, also the size of the sensor array is reduced.

In an embodiment, the plurality of modular recording sites is arranged along an axial direction and forms an array along the axial direction. An extension of the base along a first perpendicular direction perpendicular to the axial direction is at most an extension of the plurality of modular recording sites along the first perpendicular direction. An extension of the base along a second perpendicular direction perpendicular to the axial direction is at most an extension of the plurality of madder recording sites along the second perpendicular direction. This means, for example, that the cross-section perpendicular to an axis from the base through all modular recording sites (through the plurality of modular recording sites) to the last modular recording site does not have to change. This has the advantage that one can choose an arbitrary number of modular recording sites for the plurality of modular recording sites of the sensor array without influencing the cross-section of the base. Thus, the base can, for example, have the same cross section as each of the modular recording sites of the plurality of modular recording sites. Thus, it is possible to bury the base completely in the tissue. Thus, the sensor array can be placed deeper into the tissue and the invasive surgical procedure may be minimized. This embodiment does not mean that the size of the base does not change with the number of modular recording sites. The size of the base, for example, is able to change (slightly) in one dimension.

In an embodiment, a cross section of the plurality of modular recording sites in a plane perpendicular to an axial extension of the sensor array is independent of the number of modular recording sites. This can mean that the cross-section of each modular recording site does not change when more and more modular recording sites are appended to the sensor array but it can be possible to change the cross-section of each modular recording site of the plurality of modular recording sites if it is needed for the surgical procedure to have a sensor array which has, for example, a decreasing cross-section from the base over the plurality of modular recording sites to the last modular recording site. Although embodiments allow for a small base even at high numbers of modular recording sites, the size of the base may change with the number of modular recording sites. The size of the base can, for example, change (slightly) in one dimension, when increasing the number of modular recording sites.

In an embodiment, the sensor array comprises one or more columns comprising the plurality of modular recording sites. The modular concept allows the realization of any arrangement of the plurality of modular recording sites, such as in the form a two-dimensional array or a needle having one or multiple columns. The advantage of the modular concept of a plurality of modular recording sites is that the arrangement of each modular recording site of the plurality of modular recording sites with respect to each modular recording site is very flexible. Thus, for example, a sensor array with two columns can be realized. Therefore, the sensor array can record signals from a greater area. Since no global analog signal routing is present and due to high modularity of the design, a longer probe or any application-specific modification of the probe geometry would deliver identical performance.

In an embodiment, the base comprises a wired output interface for providing the probe signal. A number of channels of the wired output interface are independent of the number of modular recording sites and independent of the cross-section of the plurality of modular recording sites in a plane perpendicular to an axial extension of the sensor array. With this implementation, the complexity of the sensor array can be reduced. The reason for the reduction of the complexity of the sensor array is, for example, that one can create a sensor array with an arbitrary number of modular recording sites but with the same wired output interface at the base to an external device.

In an embodiment, the plurality of modular recording sites is arranged between the base and a sensor array endpoint of the sensor array, wherein the sensor array forms a needle. Wherein the sensor array endpoint is a biomedical sensor array endpoint, in particular a tip. Thus, the surgical procedure to get the sensor array into tissue gets easier. With the implementation of a tip it is easier to bury the sensor array in the tissue.

In an embodiment, a modular recording site of the plurality of modular recording sites comprises a housing, the housing comprising a sensor portion for receiving the signal and comprising an insulating portion for insulating the sensor portion from a sensor portion of the housing of an adjacent modular recording site. The housing may be biocompatible and therefore, the sensor array can be buried in the tissue without complications. With an insulating portion between two modular recoding sites it is possible to separate a received signal from one modular recording site from a received signal from another modular recording site. With an insulating portion it may be prevented that a received signal by one modular recording site jumps from one modular recording site to the others and thereby, one would not be able to localize the received signal with the sensor array. With an insulating portion one can, for example, localize the received signal by one modular recording site by the sensor array.

According to an embodiment, a modular recording site of the plurality of modular recording sites comprises a housing, the housing comprising two or more sensor portions for receiving the signal and comprising an insulating portion for insulating each sensor portion from another sensor portion of the two or more sensor portions. Each sensor portion of the two or more sensor portions can receive the signal, wherein each sensor portion, for example, generates an individual signal. The individual signals can be the same or at least partially differ from each other. Thus, for example, if the modular recording site comprises three sensor portions all three individual signals (e.g. generated by the three sensor portions, wherein the sensor portions can also be called electrodes or sensor elements, from the received signal) are the same, all differ from each other or two are the same and one differs from the other two. Thus one signal received by more than one sensor portion, can result in more than one individual signal, for example, depending on the position of the sensor portions. If a first sensor portion is, for example, arranged nearer to a source of the signal, than a second sensor portion, the first sensor portion generates according to an embodiment a first individual signal with a higher amplitude, than a second individual signal generated by the second sensor portion. By insulating the at least two sensor portions from each other, it may be prevented that the two or more sensor portions interact with each other and generate inaccurate individual sensors. Thus a very exact localization and analysis of the received signal can be achieved.

In an embodiment, each modular recording site of the plurality of modular recording sites is divided into an analog part and a digital part. The analog part and the digital part comprise a separate supply rooting. The digital part is shielded from the analog part by a first conductive element. This means, for example, that the analog part is separated from the digital part by a shield (low-impedance ground shield), configured to block (increase the robustness against) electromagnetic interferences. A second conductive element is arranged encircling a connector of the sensor element so as to shield the analog part and the digital part from the sensor element. In other words, the second conductive element is, for example, a shield that also covers the analog part and the digital part in the direction of the sensor. The analog part is configured to convert the biosignal received by the sensor element into the digital sensor signal. The analog part and the digital part are coupled for providing the digital sensor signal to the digital part. The digital part is configured to provide the digital sensor signal to the base. The whole sensor array is, for example, separated along one dimension (from the base to the last modular recording site) into a digital and an analog part with separate supply rooting and low-impedance ground shield in between, that also covers the top (respectively, a plane covering the analog part and the digital part in the direction of the sensor) to increase the robustness against electromagnetic interferences and to reduce digital noise coupling.

In an embodiment, a sensor array comprises a base for providing a probe signal and a plurality of modular recording sites. Each modular recording site of the plurality of modular recording sites is configured for receiving a signal, for converting the signal into a sensor signal and to provide the sensor signal to the base using a communication interface of the modular recording site. The communication interfaces of the plurality of modular recording sites are connected serially with respect to each other and to the base.

According to the embodiment, the received signal by each modular recording site is directly converted by each modular recording site into a digital sensor signal, thus, already the signal processing is done by each modular recording site. Thus, the base can be implemented with a small size, because few components for processing a signal are needed. With this embodiment, not only the size of the base can be reduced, but also the complexity of the sensor array can be low and an arbitrary number of modular recording sites can be contacted and read out at the same time.

The sensor array is based on the same considerations as the above-described sensor array. The sensor array can, by the way, be completed with all features and functionalities, which are also described with regard to the above-described sensor array.

In an embodiment of the sensor array, the sensor signal is a digital sensor signal. This has the advantage that digital sensor signals are less sensitive for electromagnetic interferences and crosstalk.

According to an embodiment a method for operating, a sensor array comprises the following steps, recording a signal with a sensor of a modular recording site of a plurality of modular recording sites of the sensor array, converting the signal into a plurality of digital sensor signals using the plurality of modular recording sites of the sensor array, providing the plurality of digital sensor signals to a base of the sensor array using communication interfaces of the plurality of modular recording sites of the sensor array, receiving the plurality of digital sensor signals from the plurality of modular recording sites of the sensor array with the base of the sensor array, processing of the plurality of digital sensor signals by the base of the sensor array so as to obtain a probe signal and providing the probe signal by the base of the sensor array for a remote device.

The method is based on the same considerations as the above-described sensor arrays.

The method can, by the way, be completed with all features and functionalities, which are also described with regard to the sensor arrays.

According to an embodiment a computer program comprising a program code for performing, when running on a computer, a method as described above, is created.

BRIEF DESCRIPTION OF THE DRAWINGS

Embodiments of the present invention will be detailed subsequently referring to the appended drawings, in which:

FIG. 2a shows a schematic block diagram of a neuronal probe with a tip according to an embodiment of the present invention;

FIG. 2b shows a schematic perspective view of the neuronal probe shown in FIG. 2a;

FIG. 3a shows a schematic block diagram of a neuronal probe with shield according to an embodiment of the present invention;

FIG. 3b shows a schematic perspective view of the neuronal probe shown in FIG. 3a;

FIG. 5a shows a circuit diagram of a modular recording site with an analog-digital converter according to an embodiment of the present invention;

FIG. 5b shows circuit diagrams of components (a Gm-C integrator, a latched comparator and an output latch) of a modular recording site according to an embodiment of the present invention;

FIG. 10a shows a schematic view of a neuronal probe according to conventional technology;

FIG. 10b shows a schematic view of a neuronal probe according to an embodiment of the present invention;

FIG. 11 shows a schematic view of a neuronal probe according to conventional technology;

DETAILED DESCRIPTION OF THE INVENTION

Figure 1:
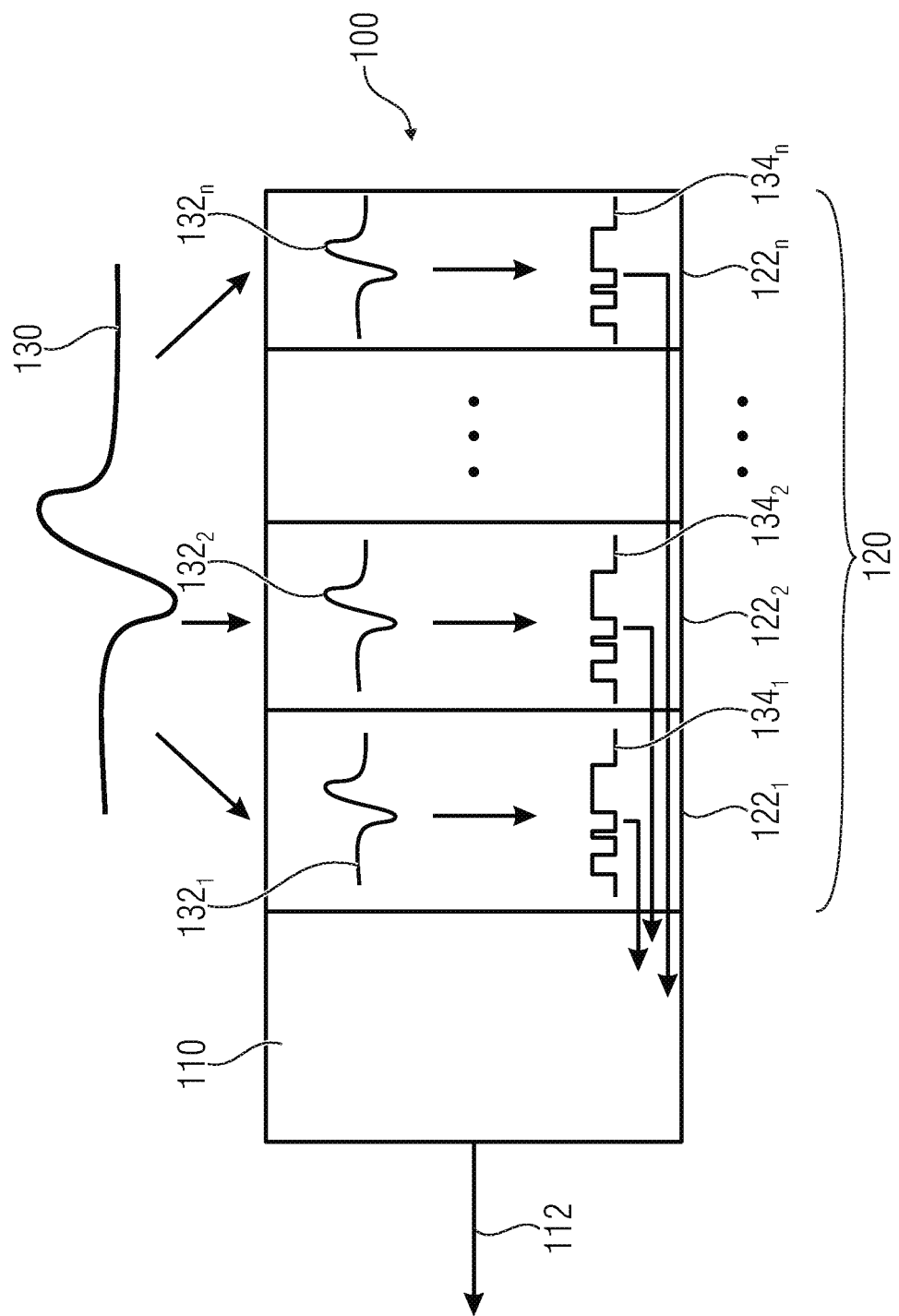
FIG. 1 shows a schematic view of a neuronal probe according to an embodiment of the present invention.

Equal or equivalent elements or elements with squat or equivalent functionality are denoted in the following description by equal or equivalent reference numerals even if occurring in different figures.

In the following description, a plurality of details is set forth to provide a more thorough explanation of embodiments of the present invention. However, it will be apparent to those skilled in the art that embodiments of the present invention may be practiced without these specific details. In other instances, well known structures and devices are shown in block diagram form rather than in detail in order to avoid obscuring embodiments of the present invention. In addition, features of the different embodiments described hereinafter may be combined with each other, unless specifically noted otherwise.

In the following, reference is made to embodiments of the present invention. Embodiments will be described in connection with neuronal probes as one possibility of implementing the present invention. Without any limitation, the description given hereinafter also relates to other sensor arrays, in particular biomedical sensor arrays. Examples for such biomedical sensor arrays are optical sensor arrays which may be used in connection with a retina of a human or animal. E.g., such a sensor array may be configured for receiving a signal. Although, in the following the described examples may refer to biosignals as the signal received by a modular recording site, the examples are not limited hereto but relate in general to other types of analogue signals such as, e.g., an optical signal or an electrical signal. A biosignal may be any signals in living beings that can be continually measured and monitored. The term biosignal may be used to refer to bioelectrical signals, but it may refer to both, electrical (e.g., electrochemically triggered) and non-electrical signals such as electrochemical signals or optical signals. A biosignal may in particular be or at least comprise an electrical signal, a signal being based on a biochemical reaction and/or an optical signal or stimulus. The sensor array may detect such a biosignal and may provide for a sensor signal based thereon. Thus, although the described examples may refer to neuronal probes which may be configured for receiving a neuronal signal, the examples are not limited hereto.

FIG. 1 shows a schematic view of a neuronal probe 100 according to an embodiment of the present invention. The neuronal probe 100 comprises a base 110, a biomedical sensor base, in particular a neuronal probe base, configured for providing a probe signal 112. The neuronal probe 100 also comprises a plurality 120 of modular recording sites. The plurality 120 of modular recording sites comprises modular recording sites $122_1$ to $122_n$. The sub-index n is, for example, an integer of at least 2, advantageously at least ten and more advantageously at least 50 such as 50, 70, 100 or more, e.g. 144, wherein it is also possible that the sub-index n is an arbitrary integer above 144. For convenience, each modular recording site will be identified by $122_e$. Each modular recording site $122_e$ of the plurality 120 of modular recording sites is configured for receiving a neuronal signal or biosignal 130, wherein each modular recording site $122_e$ can receive neuronal signals $132_1$ to $132_n$. The neuronal signals $132_1$ to $132_n$ can comprise at least two of the neuronal signals $132_1$ to $132_n$, which are similar or the same or all neuronal signals $132_1$ to $132_n$ are different with respect to each other. Each modular recording site $122_e$ of the plurality 120 of modular recording sites is configured for converting the received neuronal signal $132_1$ to $132_n$ into a digital sensor signal $134_1$ to $134_n$. Each modular recording site $122_e$ of the plurality 120 of modular recording sites is configured for providing the digital sensor signal $122_1$ to $122_n$ to the base 110. The base 110 is configured for receiving a plurality of digital sensor signals $122_1$ to $122_n$ from the plurality 120 of modular recording sites and to process the plurality of digital sensor signals $134_1$ to $134_n$ so as to provide the probe signal 112.

The neuronal probe 100 may be used as a tissue penetrating probe for high density deep-brain recording of in vivo neural activity and overcomes a limitation by the level of electronic integration on the probe shaft. Active probes are, in conventional technology, used to improve the signal quality and reduce parasitic effects in situ, but still need to route these signals from the electrodes to a base where the readout electronics is located on a large area [4, 6]. The neuronal probe 100 comprises the conversion of the received neuronal signal $132_1$ to $132_n$ into a digital sensor signal $134_1$ to $134_n$ in each modular recording site $122_e$ of the plurality 120 of modular recording sites, so that the base 110 does not need this component and therefore, the base 110 can be implemented on a small area.

FIG. 2a shows a block diagram of a neuronal probe 200 and FIG. 2b shows a schematic view of a neuronal probe 200.

The neuronal probe 200 in FIG. 2a comprises a base 210, a plurality 220 of modular recording sites and, for example, a tip 230. Each modular recording site $224_1$ to $224_n$ of the plurality 220 of modular recording sites comprises a sensor element $222_1$ to $222_n$, an in-situ analog-to-digital converter $226_1$ to $226_n$ and a bi-directional serial digital data bus $228_1$ to $228_n$. The base 210 of the neuronal probe 200 comprises a reference 212, an electrical power supply 214, a digital interface/control unit 216 and a peripheral interface/contacting 218 (pads), wherein the reference 212, for example, provides a ground potential or an arbitrary reference potential for each of the modular recording sites $224_1$ to $224_n$, the electrical power supply 214 provides power for each of the modular recording sites $224_1$ to $224_n$ and the electrical power supply 214 forms with the reference 212 a differential input for the analog-to-digital converter $226_1$ to $226_n$ and the digital interface control unit 216 is connected to each bi-directional serial digital data bus $228_1$ to $228_n$ of each of the modular recording sites $224_1$ to $224_n$ and configured for providing configuration data to the plurality 220 of modular recording sites allowing for adjusting of, for example, the operation of each of the in-situ analog-to-digital converter $220_1$ to $226_n$ of each of the modular recording sites $224_1$ to $224_n$. The main function of the tip 230 is, for example, to get easier into tissue. The plurality 220 of modular recording sites is, for example, able to receive a neuronal signal with different sensor elements $222_e$ to $222_n$.

FIG. 2a shows a schematic configuration of a neuronal probe 200 as a modular readout circuit. The modular recording sites $224_1$ to $224_n$ are an arbitrary number and may comprise sensors or sensor elements $222_1$ to $222_n$, optionally electrodes (which receive neuronal pulses as a voltage), optical sensors or chemical sensors. Each modular recording site $224_1$ to $224_n$ is configured to receive a neuronal signal over the sensor element $222_1$ to $222_n$, to convert the received neuronal signal with the in-situ analog-to-digital converter $226_1$ to $226_n$ into a digital sensor signal and to transfer this digital sensor signal in a bi-directional serial digital data bus $228_1$ to $228_n$ to a digital interface/control unit 216 of the base 210. The digital interface/control unit 216 is configured for receiving a plurality of digital sensor signals from the plurality of modular recording sites $224_1$ to $224_n$ over a bi-directional serial digital data bus $228_1$ to $228_n$ and to process the plurality of digital sensor signals so as to provide a probe signal to a peripheral interface/contacting 218, whereby the peripheral interface/contacting 218 is configured to make a connection with an external device and send the probe signal to the external device.

FIG. 2b shows a schematic view of a neuronal probe 200. The neuronal probe 200 comprises a plurality of modular recording sites $224_1$ to $224_n$, wherein each modular recording site $224_1$ to $224_n$ comprises a sensor element $222_1$ to $222_n$. The sensor elements $222_1$ to $222_n$ are connected to electronics 240 under each sensor element $222_1$ to $222_n$ with a sensor contact area 250. At one end of the neuronal probe, the neuronal probe comprises pads 260 which are, for example, used as a peripheral interface/contacting 218. With the peripheral interface/contacting 218 the probe is connected to a cable and by that to a remote device. The sensor elements $222_1$ to $222_n$ can, for example, receive a neuronal signal and transfer the neuronal signal over the sensor contact area 250 to the electronics 240 under the sensor elements $222_1$ to $222_n$. The electronics 240 under each sensor element $222_1$ to $222_n$ can, for example, process the received neuronal signal and convert the neuronal signal into a (digital) sensor signal.

FIG. 3a shows a block diagram of a neuronal probe 300 and FIG. 3b shows a schematic view of the neuronal probe 300.

The neuronal probe 300 of FIG. 3a comprises a tip 310 which has, for example, the same function as the tip 230 in FIG. 2a. A plurality of modular recording sites $320_1$ to $320_n$ which may implement the same function as each of the modular recording sites $224_1$ to $224_n$ of FIG. 2a and FIG. 2b. The neuronal probe 300 further comprises a base 330 which can, for example, have the same functionality as the base 210 of FIG. 2a or the base 110 of FIG. 1. Each modular recording site $320_1$ to $320_n$ comprises a sensor element $322_1$ to $322_n$. The sensor elements $322_1$ to $322_n$ can, for example, have the same functionality as the sensor elements $222_1$ to $222_n$ of FIG. 2a and FIG. 2b. Each modular recording site $320_1$ to $320_n$ also comprises an integrator $324_1$ to $324_n$, a quantizer $325_1$ to $325_n$, a counter $328_1$ to $326_n$ and a bi-directional serial digital data bus 328, wherein the bi-directional serial digital data bus 328 can, for example, have the same functionality as the bi-directional serial digital data bus $228_1$ to $228_n$ of FIG. 2a. The bi-directional serial digital data bus 328 can for each modular recording site $320_1$ to $320_n$ comprise a communication Interface 328, wherein the communication Interface 328 can either be in a configuration made $328_{1s}$ to $328_{ns}$ or in a normal operating mode $328_{1b}$ to $328_{nb}$.

In other words, a digital part 350 of each modular recording site $320_1$ to $320_n$ of the plurality of modular recording sites comprises, for example, the communication interface $328_1$ to $328_n$ which is connected to its neighboring nodes (for example the communication interfaces $328_1$ to $328_n$ of each neighboring modular recording site) by a serial interface. In that way, the converted results (for example, the digital sensor signals) can be linked to the results of the neighboring nodes and can be carried to an external terminal (for example the base 330 or an external device connected to the base) of the overall system (for example, the neuronal probe 300). In that way, for example, the number of connections from one modular recording site $320_1$ to $320_n$ of the plurality of modular recording sites to a neighboring modular recording site $320_1$ to $320_n$ of the plurality of modular recording sites (the modular recording site $320_1$ to $320_n$ can, for example, also be understood as a sensor channel) is kept as low as possible and no analog signal (for example the received neuronal signal by each modular recording site $320_1$ to $320_n$) susceptible to interferences is carried to the outside (for example to the base or to an external device connected to the base) or from the base 330 (for example the outside) into a modular recording site $320_1$ to $320_n$ (for example also understood as a sensor node). Since all neuronal signals (this may be an electrode signal or a sensor signal) are digitized (this means, for example, that each neuronal signal received by a modular recording site $320_1$ to $320_n$ of the plurality of modular recording sites $320_1$ to $320_n$ is converted into a digital sensor signal) directly on-site (for example on each modular recording site $320_1$ to $320_n$) the neuronal probe 300 (respectively, the system) needs only a very small number of lines to the outside (this can, for example, include lines from the base 330 to an external device but it can also include, for example, lines from each modular recording site $320_1$ to $320_n$ to the base 330). Thus, the neuronal probe 300 not only reduces the complexity but also the size of the base 330 and shaft (for example, the plurality of modular recording sites $320_1$ to $320_n$ with the tip 310) of the neuronal probe 300, because only a reduced number of lines from each modular recording site $320_1$ to $320_n$ of the plurality of modular recording sites $320_1$ to $320_n$ is needed to transfer a digital sensor signal to the base 330. The serial connection of the communication interfaces $323_1$ to $328_n$ of the plurality of modular recording sites $320_1$ to $320_n$ with respect to each other and to the base also enables the neuronal probe to contact an arbitrary number of modular recording sites $320_1$ to $320_n$ (respectively, sensor nodes).

Each of the digital sensor signals from each of the modular recording sites $320_1$ to $320_n$ can be transferred to the base 330 as a combined sensor signal. Each modular recording site $320_1$ to $320_n$, for example, provides the converted neuronal signal as a digital sensor signal to the bi-directional serial digital data bus 328. Then the digital sensor signal is transferred by the digital data bus 328 as a combined sensor signal, of all digital sensor signals of the plurality of modular recording sites, to the base 330, where the base 330 processes the combined sensor signal to provide a probe signal.

According to an embodiment, the neuronal probe 100, 200 and 300 shown in FIG. 1, FIG. 2 and FIG. 3 can be seen as a sensor array configured for receiving analog signals, like an optical signal or an electrical signal, as an alternative or in addition to the described analog biosignal which may comprise, by way of non-limiting example, a neuronal signal, and is therefore called sensor array 300 in the following description regarding FIG. 3.

The sensor array 300 is according to an embodiment a Pixel-Level ADC (ADC=analog digital converter), which represents, for example, an optical sensor with a conversion of an analog signal to a digital signal at each modular recording site $320_1$ to $320_n$. The inventive sensor array 300 is optimized with regard to known optical sensors in terms of a self-sufficient analog-to-digital-conversion. Known sensors are based on an electric current (photodiode) to time conversion (time interval of a pulse). The time interval of a pulse respectively the time needed to reach a threshold is measured in known sensors at all sensor knots or nodes at the same time, which results in a parallel link between the sensors and no serial link is possible. A serial link like in an embodiment of the sensor array 300 will result e.g. in area-efficient and/or cheaper sensors.

The base 330 of the neuronal probe 300 may comprises a reference 331 which can, for example, have the same functionality as the reference 212 of FIG. 2a, an electrical power supply 334 which can, for example, have the same functionality as the electrical power supply 214 of FIG. 2a and a digital interface/control unit 339 which can, for example, have the same functionality as the digital interface/control unit 216 of FIG. 2a. The base 330 also comprises pads/digital four wire interface 340 which can, for example, have the same functionality as the peripheral interface/contacting 213 of FIG. 2a. The tip 310 of the neuronal probe 300 comprises, for example, a first supply buffer 312 and a second supply buffer 314.

Each converter (modular recording site $320_1$ to $320_n$) comprises a digital part 350 and an analog part 360 and is configured for minimum area consumption. The system (for example, the neuronal probe 300) is structured in a modular manner: the signal of each electrode (sensor element $322_1$ to $322_n$) is locally converted to a digital output signal independent of the neighboring electrode (sensor element $322_1$ to $322_n$).

In that way, the number of connections to a neighboring module (sensor channel/modular recording site $320_1$ to $320_n$) is kept as low as possible and no analog signals susceptible to interference are carried to the outside or from the outside into the sensor node (sensor element $322_n$ to $322_n$). Since all electrode signals (neuronal signals) are digitized (converted into a digital signal) directly on site, the system (for example, the neuronal probe 300) needs only a very small number of lines to the outside (for example, to an external device).

Each modular recording site $320_1$ to $320_n$ of the neuronal probe 300 can receive a neuronal signal with sensor elements $322_1$ to $322_n$ and convert the received neuronal signal into a digital sensor signal by first integrating the neuronal signal by the integrator $324_1$ to $324_n$ and quantization using a quantizer $325_1$ to $325_n$. With the bi-directional serial digital data bus 328, the digital sensor signal of each modular recording site $320_1$ to $320_n$ is transferred from each modular recording site $320_1$ to $320_n$ to the digital interface/control unit 339 of the base 330, where the digital sensor signal is processed by the digital interface/control unit 339 into a probe signal, wherein the probe signal is transferred over the pads/digital four wire interface 340 to an external device.

The whole probe (neuronal probe 300) is separated along its length into a digital 350 and an analog part 360 with separate supply routing and optionally a low-impedance ground shield 390 in between, that also covers the top to increase the robustness against EMI (electromagnetic interferences) and to reduce digital noise coupling.

The supply routing can be realized with the electrical power supply 334. The supply routing for the analog part 360 comprises, for example, a voltage $V_{DD,A}$ 335 with an optional supply buffer $335_s$ and a ground voltage $V_{SS}$ 336. The supply routing for the digital part comprises, for example, a voltage $V_{DD,D}$ 337 with the ground voltage $V_{SS}$ 336. The digital part 350 may be connected to its neighboring node (neighboring recording site $320_1$ to $320_n$) by a serial interface (communication interfaces $328_1$ to $328_n$). In that way, the converted results may be linked to the results of the neighboring node (neighboring modular recording site $320_1$ to $320_n$) and may be carried to the external terminal (for example an external device or the base 330) to the overall system. Configuration data can be carried in a linked manner to each sensor node (modular recording site $320_1$ to $320_n$) via the same interface (communication interfaces $328_1$ to $328_n$) for switching the node (for example, the modular recording site $320_1$ to $320_n$) on and off or for changing its scaling, for example. The base 330 includes, for example, a reference transistor 332 providing the global voltage biasing $V_{BIAS}$ to all recording sites (modular recording sites $320_1$ to $320_n$) and a finite-state-machine that allows to switch between a configuration mode and a normal operating mode (readout modes) and forwards the internal data (for example the digital sensor signal) and configuration chains to the external unit (for example, an external device). The switching (of the communication interfaces $328_1$ to $328_n$) between the configuration mode $328_{1s}$ to $328_{ns}$ and the normal operation mode $328_{1b}$ to $328_{nb}$ is controlled, for example, with a separate control signal. In the configuration mode $328_{1a}$ to $328_{na}$, settings may be readout of a storage, which is, for example, transferred over the bi-directional serial digital data bus 328 and can be adapted by each modular recording site $320_1$ to $320_n$, while in the normal operation mode $328_{1b}$ to $328_{nb}$ the digital output (the digital sensor signal) of the converter (modular recording site $320_1$ to $320_n$) will, for example, be written in the storage. The storage may be a volatile or non-volatile storage and may comprise, for example, a plurality of transistor elements for storing information. According to embodiments, the configuration data in the configuration mode $328_{1a}$ to $328_{na}$ and the digital data in the normal operation mode $328_{1b}$ to $328_{nb}$ may be transmitted between each modular recording site $320_1$ to $320_n$ and the base 330 without using a storage by using the bi-directional serial digital data bus 328 directly.

On the digital side 350, no global signals have to be routed: the chain signal, as well as the clock, may be forwarded from one block (bi-directional serial digital data bus 328) to the next one. The clock is slightly delayed from each modular recording site $320_1$ to $320_n$ to each modular recording site $320_1$ to $320_n$ to spread digital supply noise and reduce peak current consumption. The recording sites (modular recording sites $320_1$ to $320_n$) are grouped into blocks of two ADCs (analog-to-digital converter), one connected to the forward chain 352 and one to the backward chain 354 and clock. In the analog part 360, there may be only two global reference lines throughout the probe, i.e., the body reference voltage $V_{BODY}$ 333a and $V_{BIAS}$ 333b. The bias voltage (referenced to $V_{DD}$) is routed with large parasitic capacitances to the supply 334 to enhance noise rejection from external sources.

In other words, the modular recording sites $320_1$ to $320_n$ are, for example, grouped into blocks of two modular recording sites (ADCs respectively, analog-to-digital converters comprising, for example, each of the integrators $324_1$ to $324_n$ and each of the quantizer $325_1$ to $325_n$), wherein one modular recording site comprising a first ADC is connected to the forward chain 352 and forward clock and the other modular recording site comprising a second ADC is connected to the backward chain 354 and backward clock. Thus, the serial interfaces (communication interfaces $328_1$ to $328_n$) of every second modular recording site are, for example, connected/coupled to a first chain (for example forward chain 352) and the serial interfaces of all other modular recording sites are connected/coupled to a second chain (for example backward chain 354). The first chain and the second chain are coupled to the base such that the digital sensor signal is transferred to the base.

The analog-digital converter (for example, the integrator $324_1$ to $324_n$ coupled with the quantizer $325_1$ to $325_n$) may be configured with a differential input in order to be largely robust against interferences of the supply voltage (for example, the supply voltage $V_{DD,A}$ 335 with the ground $V_{SS}$ 336 of the electrical power supply 334). Apart from the supply voltage (for example, the electrical power supply 334), two further global lines (for, example, joints) may be used and may be shared by all sensor nodes (modular recording sites $320_1$ to $320_n$);

The control voltage (for example, the reference voltage $V_{BIAS}$ 333b): each circuit needs, for example, internally a certain number of constant reference potentials and setting currents. All currents and potentials are, for example, derived from the global adjusting voltage (for example, the control voltage $V_{BIAS}$ 333b) which is distributed to all sensor nodes (modular recording sites $320_1$ to $320_n$) as global line. Since it is a global line to which all sensor modules (modular recording sites $320_1$ to $320_n$) are connected, the same may be provided with large parasitic capacitance. This has a positive effect on possible coupling of noise via this line. Additionally, noise (for example, on the control voltage $V_{BIAS}$ 333b) is suppressed by the differential readout principle. This control voltage (for example, the reference voltage $V_{BIAS}$ 333b) may be used for testing, but in principal it (for example, the reference voltage $V_{BIAS}$ 333b) does not necessarily have to be a global connection and the function can, for example, be implemented under each electrode (sensor element $322_1$ to $322_n$).

The reference voltage (for example, the reference voltage $V_{BODY}$ 333a): One side of the differential input is, for example, connected to the sensor (electrode/sensor element $322_1$ to $322_n$) while the second input is, for example, connected to a reference voltage (for example, the reference voltage $V_{BODY}$ 333a). Possible interferences on $V_{BODY}$ (reference voltage $V_{BODY}$ 333a) can be detected equally on all sensor nodes (modular recording sites) and can hence be filtered put in digital post-processing.

Since even the largest neuronal signals are only in the range of some tens of millivolts and the needed linearity is low, a direct conversion using, for example, a continuous-time gm-C based incremental delta-sigma analog-to-digital converter (for example, the integrator $324_1$ to $324_n$ coupled with the quantizer $325_1$ to $325_n$) under each electrode (sensor element $322_1$ to $322_n$) may be implemented using a first-order modulator allowing the implementation on a minimal silicon area, since only one integrator $324_1$ to $324_n$ and capacitor and no accurate time constants, thus no local biasing, are needed. Decimation may be accomplished using a simple ripple counter $326_1$ to $326_n$. The output of the single branch OTA-C integrator $324_1$ to $324_n$ is, for example, connected to the quantizer $325_1$ to $325_n$, i.e., comparator and output latch, driving the switches for the current feedback.

In the following a concrete example of a neuronal probe according to an embodiment is given, such as the neuronal probe 300. The example includes several concrete values of parameters used for implementing the neuronal probe. The values are to be understood as nonlimiting example only and therefore they do not limit the embodiments but are merely suitable for a better understanding of the present invention. It is clear that by using further, different or other components other values may be obtained such as different voltages, currents and/or data rates.

The digital part 350 of the ADC (analog-to-digital converter) consists, for example, of a decimator, i.e., ripple counter $326_1$ to $326_n$, two registers for the 11b (11 bit) conversion result and a 2b (2 bit) configuration register. According to an example the ADC may run for 1024 cycles delivering a 10b result. Before resetting the OTA, the OTA output (for example, the output of the integrator $324_1$ to $324_n$) and the counter $326_1$ to $326_n$, the results may be transmitted using the data bus. For example, the last result of the comparator which represents the final conversion error may be appended as the eleventh bit to the 10 bit result and the obtained 11 bit may be put on the data chain. For example, the bit sequence may be stored in the storage of the bi-direction serial digital data bus 328. Alternatively or in addition, the bit sequence of the digital sensor signs of each modular recording site $320_1$ to $320_n$ may directly be transmitted using the bi-directional serial digital data bus 328. The delayed clock of a following cell (modular recording site $320_1$ to $320_n$) is used for a latch to avoid timing violations between the latch and the comparator. During readout, the digital data (the plurality of digital sensor signals) is shifted through the modular recording sites $320_1$ to $320_n$ and the neuronal probe 300 uses two possibly chains (the forward chain 352 and the backward chain 354), each of them may use the same or different data rate such as at least 15 Mbit/s or at least 20 Mbit/s such as 20.48 Mbit/s. For example both chains (the forward chain 352 and the backward chain 364) may use a bit rate of 20.48 Mbit/s, i.e., $f_s$=20.48 MHz. The FSM in the base 330 may combine the outputs of both chains into a single data stream, e.g., by time multiplexing which yields, for example, 40.96 Mbit/s at the front-end in the given example. The base 330 may be a low power element and may consume less than 1 W, less than 100 mW or even less than 100 µW, e. g., 37 µW and the power consumption per recording site (modular recording site $320_1$ to $320_n$) may result to less than 1 W, less than 100 mW or even less than 100 µW, e. g., 39.14 µW, of which less than 1 W, less than 100 mW or even less than 100 µW, e.g., 12.77 µW are consumed by the analog part 360.

The 11b ADCs (for example, the integrator $324_1$ to $324_n$ coupled with the quantizer $325_1$ to $325_n$) may be designed to optimize noise performance per area, therefore as much area as possible is dedicated to the noise critical components, i.e., the input (the dedicated area should be less than 1000 µm², or less than 500 µm², or less than 200 µm² such as 171 µm² in the given example) and the load transistors (the dedicated area should be less than 1000 µm², or less than 500 µm², or less than 200 µm² such as 144 µm² in the given example). Only a small area is, for example, dedicated to the feedback current sinks, which are derived from the global bias line. The feedback current determines the full-scale (FS) of the ADC (for example, the integrator $324_1$ to $324_n$ coupled with the quantizer $325_1$ to $325_n$) which can be configured to one of three different scopes, for example, one scope of ±15 mV, a second scope of ±30 mV and a third scope of ±55 mV or one scope of ±13 mV, a second scope of ±25 mV and a third scope of ±50 mV, or in one scope of ±12 mV, a second scope of ±23 mV and a third scope of ±46 mV, such as ±11.25 mV, ±22.5 mV or ±45 mV.

FIG. 3b shows a system-level schematic with 3D view of the neuronal probe 300. The housing of the neuronal probe 300 comprises optionally a passivation layer (externally covering, the housing and providing electrical insulation for the housing. The passivation layer may spare one or more regions allowing electrical signals passing the housing, e.g., at a location of pads 340 and/or electrodes), only the pad 340 (in FIG. 3b, only one pad is shown but the neuronal probe 300 can also be implemented with more than one pad 340) and the electrodes (sensor elements $322_1$ to $322_n$) may be free of a passivation layer. The signal chain of the readout electronics is getting small by omitting pre-amplification, amplification and filtering and can be replaced by a local analog-to-digital conversion of the sensor signals (neuronal signals). Thereby, an analog-to-digital converter can be implemented below each sensor (electrode/sensor element $322_1$ to $322_n$) directly on the shaft. The sensor elements $322_1$ to $322_n$ may be coupled to the electronics under each sensor element $322_1$ to $322_n$ by an electrode contact 323.

Each modular recording site $320_1$ to $320_n$ may be divided into an analog part 360 and a digital part 350. The digital part 350 may be shielded from the analog part 360 by a first conductive element 390, wherein the conductive element is configured to block electromagnetic interferences. The conductive element can, for example, be a low-impedance ground shield. A second conductive element 392 is arranged encircling a connector (electrode contact 323) of the sensor element $322_1$ to $322_n$ so as to shield the analog part 360 and the digital part 350 from the sensor element $322_1$ to $322_n$. Under each sensor element $322_1$ to $322_n$ the reference 331 can be implemented with the control voltage $V_{BIAS}$ 333b and the reference voltage $V_{BODY}$ 333a. The electrical power supply 334 can be implemented as, for example, the analog supply voltage $V_{DD,A}$ 335 and the ground voltage $V_{SS}$ 336.

At least a part of the analog part 360 and at least a part of the digital part 350 are, for example, covered by a sensor element $322_1$ to $322_n$ configured for receiving the neuronal signal. In an embodiment the sensor element $322_1$ to $322_n$ covers the digital part 350 and the analog part 360 centric, but it is also possible, that the sensor element $322_1$ to $322_n$ covers only the digital part 350 or only the analog part 360.

In this embodiment, a modular and scalable architecture of a needle probe is realized, which, instead of routing or pre-buffering noise-sensitive analog signals along the shaft, integrates, for example, analog-to-digital conversion under each electrode (sensor element $322_1$ to $322_n$). An area used for such integration may be arbitrary and be influenced by the functionality to be integrated. For example, an area of less than 200×200 µm², less than 150×150 µm² or less than 100×100 µm², such as, for example, 70×70 µm² may be used. The design eliminates the need for any additional readout circuitry at the top of the probe (for example, neuronal probe 300) and connects with a digital 4-wire interface 340. The neuronal probe 300 may be implemented as reconfigurable 11.5 mm neuronal probe (but it is also possible to have larger probes of more than 11.5 mm, more than 14 mm or also more than 20 mm) features a constant width 370 of 70 µm (The width 370 is, for example, smaller than 100 µm, smaller than 90 µm or smaller than 75 µm) and thickness 380 (The thickness 380 is, for example, smaller than 100 µm, smaller than 80 µm or smaller than 60 µm) of 50 µm from top to bottom (for example, from the last modular recording site $320_n$ to the first modular recording site $320_1$ or to the base 330 along an axial extension of the array) for minimal tissue damage with, for example, 144 integrated recording sites (modular recording sites $320_1$ to $320_n$) and can be fully immersed in tissue for deep-brain recording applications.

The plurality of modular recording sites $320_1$ to $320_n$ is arranged along an axial direction and forms an array along the axial direction. An extension along a first perpendicular direction perpendicular to the axial direction is understood as the width 370 and an extension along a second perpendicular direction perpendicular to the axial direction understood as the thickness 380.

In an embodiment, the plurality of modular recording sites $320_1$ to $320_n$ is, for example, arranged along an axial direction and forms an array along the axial direction. An extension of the base 330 along a first perpendicular direction perpendicular to the axial direction is, for example, at most an extension of the plurality of modular recording sites $320_1$ to $320_n$ along the first perpendicular direction. An extension of the base 330 along a second perpendicular direction perpendicular to the axial direction is, for example, at most an extension of the plurality of modular recording sites along the second perpendicular direction.

In other words, an elongation of the base 330 in a direction of an axis of the plurality of modular recording sites $320_1$ to $320_n$ may be not bigger than an elongation of the plurality of modular recording sites $320_1$ to $320_n$ in a direction of an axis of the plurality of modular recording sites $320_1$ to $320_n$. An elongation of the base 330 in a direction perpendicular to an axis of the plurality of modular recording sites $320_1$ to $320_n$ may be not bigger than an elongation of the plurality of modular recording sites $320_1$ to $320_n$ in a direction perpendicular to an axis of the plurality of modular recording sites $320_1$ to $320_n$. In other words, the cross-section perpendicular to an axis from the base through all modular recording sites $320_1$ to $320_n$ (through the plurality of modular recording sites $320_1$ to $320_n$) to the last modular recording site $320_n$ does not have to change. This has the advantage that one can choose an arbitrary number of modular recording sites $320_1$ to $320_n$ for the plurality of modular recording sites $320_1$ to $320_n$ of the neuronal probe without influencing the cross-section of the base 330. Thus, the base 330 can, for example, have the same cross-section as each of the modular recording sites $320_1$ to $320_n$ of the plurality of modular recording sites $320_1$ to $320_n$. Thus, it is possible to bury/immerse. the base 330 completely in the tissue. Thus, the neuronal probe 300 can be placed deeper into the tissue and the invasive surgical procedure may be minimized.

The modular concept allows the realization of any arrangement of sensor nodes (modular recording sites $320_1$ to $320_n$), such as, for example, in the form of a two-dimensional array of a needle having one or multiple columns. Each modular recording site $320_1$ to $320_n$ may be arranged and connected to each other in at least one row or column. When referring again to FIG. 3b, the neuronal probe 300 may comprise a single row of a plurality of modular recording sites, being arranged along an axial direction. According to embodiments, a neuronal probe 300 may comprise more than one row or line of modular recording sites $320_1$ to $320_n$. Within one row or column, the modular recording sites $320_1$ to $320_n$ may be arranged serially to each other so as to avoid parallel communication and to thereby allow for small communication entities. Thus, an axial extension of the neuronal probe 300 along the axial direction may at least be influenced by a number of modular recording sites $320_1$ to $320_n$ arranged along that direction. In contrast, the number of modular recording sites $320_1$ to $320_n$ may have low or even no impact on an extension of the row/column of the neuronal probe 300 along one or more directions perpendicular to the axial direction.

Since only the digital data and no sensitive signals are carrier along the shaft, a low amount or even no crosstalk can be measured between the sensors (for example, between each sensor element $322_1$ to $322_n$) or between each modular recording sites $320_1$ to $320_n$ and there is high robustness with respect to external interference sources such as light sources or electromagnetic fields.

The number of lines to the outside may be independent of the number of electrodes (sensor elements $322_1$ to $322_n$) and/or sensor modules (for example, the number of modular recording sites $320_1$ to $320_n$), respectively, and/or independent on the width 370 of the shaft.

Since the base 330 of the needle may have the same width 370 as the shaft, the same can be introduced into tissue beyond the length of the shaft without causing additional damage. Thus, deeper brain areas can be measured when compared with conventional needles.

The neuronal probe 300 can, for example, represent a fully immersible deep-brain neuronal probe with modular architecture and a Delta-Sigma ADC (analog-to-digital converter) integrated under each electrode for parallel readout of, for example, 144 recording sites.

Figure 3C:
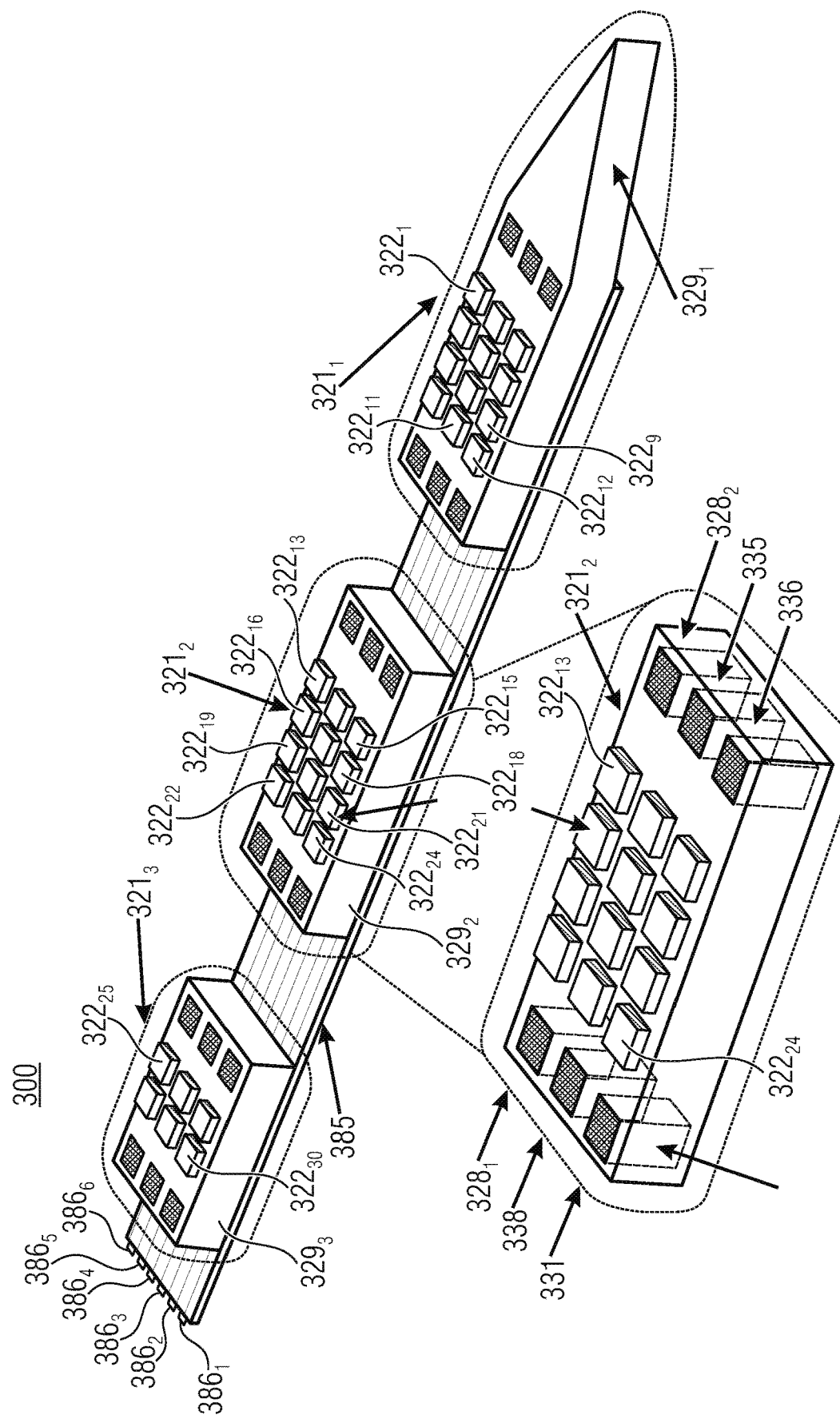
FIG. 3c shows a schematic perspective view of a segmented neuronal probe according to an embodiment of the present invention.

FIG. 3c shows a schematic 3D view of a segmented probe 300 representing an embodiment of the inventive sensor array, wherein the segmented probe 300 can comprise features and functionalities of the neuronal probe 300 shown in FIG. 3a and FIG. 3b. The segmented probe 300 shown in FIG. 3c differs from the neuronal probe 300 in FIG. 3a and FIG. 3b with regard to a positioning of modular recording sites and an arrangement of sensor elements (the sensor elements can also be described as sensor portions or electrodes), as described further below. In FIG. 3c equal or equivalent elements or elements with equal or equivalent functionality, compared to elements shown in FIG. 3a and FIG. 3b, are denoted by equal or equivalent reference numerals even if occurring in different figures.

According to an embodiment the segmented probe 300 shown in FIG. 3c comprises a number of at least two, at least three, at least four or even a higher number such as 10, 20 or the like of segments $321_1$ to $321_3$, wherein each segment $321_1$ to $321_3$ may comprise a number of sensor elements $322_1$ to $322_{30}$. Although being illustrated, for example, as comprising a number of 12 sensor elements $322_1$ to $322_{12}$ or $322_{13}$ to $322_{24}$ being arranged in a 3×4 configuration or a number of 6 sensor elements $322_{25}$ to $322_{30}$ being arranged in a 3×2 configuration any different number of sensor elements and/or any different configuration may be implemented within the scope of the described embodiment. At a tip of the segmented probe 300 is a first segment $321_1$ positioned, then comes a second segment $321_2$, then a third segmented $321_3$, and then more segments can be arranged before, for example, a base is positioned at an end of the segmented probe 300.

According to an embodiment, the sensor array, i.e. the segmented probe 300, comprises a plurality of modular recording sites, for example, represented by the segments $321_1$ to $321_3$ or by the sensor elements $322_1$ to $322_{30}$. For example, one sensor element $322_1$ to $322_{30}$ can represent one modular recording site and/or a group of two or more sensor elements $322_1$ to $322_{30}$ can represent one modular recording site, wherein one modular recording site comprises, for example, one analog-to-digital-converter.

According to an embodiment, a first subset of the plurality of modular recording sites is arranged on a first semiconductor substrate $329_1$, and wherein an adjacent and neighboring second subset of the plurality of modular recording sites is arranged on a second semiconductor substrate $329_2$; wherein the first semiconductor substrate $329_1$ and the second semiconductor substrate $329_2$ are spaced apart from each other by a gap and electrically connected to each other by at least one conductive line $386_1$ to $388_6$. If the first segment $321_1$ represents one modular recording site, this means, for example, that the segment $321_1$ is the first subset of the plurality of modular recording sites, wherein the modular recording site comprises 12 sensor portions $322_1$ to $322_{12}$ and one analog-to-digital-converter. If a sensor element $322_{13}$ to $322_{24}$ or groups of sensor elements (e.g. 2×2, 3×1, 1×3, 3×2, etc.) represent on the second semiconductor substrate $329_2$ two or more modular recording sites, this means, for example, that the two or more modular recording sites represent the second subset. Thus, for example, the second subset on the second semiconductor substrate $329_2$ comprises 4 modular recording sites, if each modular recording site comprises 3 sensor elements $322_{13}$ to $322_{15}$, $322_{16}$ to $322_{18}$, $322_{19}$ to $322_{21}$ and $322_{22}$ to $322_{24}$ with, for example, a 3×1 configuration and wherein each of the 4 modular recording sites comprises one analog-to-digital-converter. In FIG. 3c are shown three semiconductor substrates $329_1$ to $329_3$ which are spaced apart by a gap without semiconductor substrate.

According to an embodiment, the at least one conductive line $386_1$ to $386_6$ is arranged on or in a flexible substrate 385, According to an embodiment, the segments $321_1$ to $321_3$ are arranged on the flexible substrate 385, like a flexible polymer cable. To improve the flexibility of the segmented probe 300 and to reduce possible damage to the segmented probe 300 by bending or twisting the probe, a gap between the segments $321_1$ to $321_3$ can be adjusted. The larger the gap, the more flexible is, for example, the segmented probe 300.

According to an embodiment a segment $321_1$ to $321_3$ comprises contacts, which connect each segment $321_1$ to $321_3$ to the flexible polymer cable 385, the flexible polymer cable thereby interconnecting the segments, e.g., in a serial way. According to an embodiment signals and/or a power supply is provided for each segment $321_1$ to $321_3$ by the base through the flexible polymer cable 385 and each segment $321_1$ to $321_3$ is, for example, configured to transmit signals by the flexible polymer cable 385 to the base, wherein the segments $321_1$ to $321_3$ are, for example, connected serially by the flexible polymer cable 385. Each segment $321_1$ to $321_3$ comprises, for example, a number of interfaces or contacts $328_1$, $328_2$, 331, 335, 336 and/or 338. Whilst being illustrated as having six contacts, embodiments are not limited hereto as any number of contacts, i.e., more or less, may be implemented so as to transmit signals and/or provide for power supply. For example, a first contact 331 represents a reference, e.g. a reference voltage, a second contact 338 represents a clock, a third contact $328_1$ represents a data input, a fourth contact $328_2$ represents a data output, a fifth contact 335 represents a voltage supply and a sixth contact 336 represents a ground, e.g., a ground voltage.

According to an embodiment, the segments $321_1$ to $321_3$ can comprise a CMOS silicon substrate $329_1$ to $329_3$, in which the electronics of the proposed sensor array, i.e. the segmented probe, is implemented. Optionally the six contacts or at least some of the six contacts 331, 338, $328_1$, $328_2$, 335 and/or 336 can be realized as through-silicon vies.

Figure 4A:
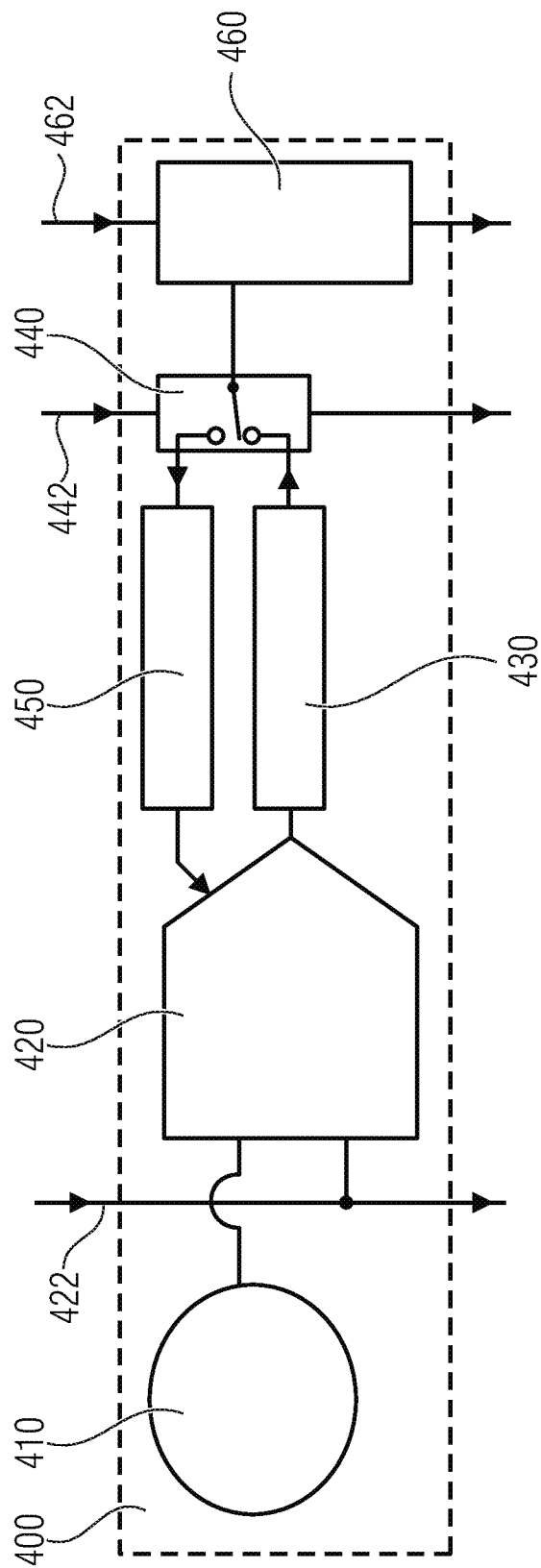
FIG. 4a shows a schematic block diagram of a modular recording site according to an embodiment of the present invention.

FIG. 4a shows a block diagram of a modular recording site 400, wherein the modular recording site 400 has the same functionality as each of the modular recording sites $122_1$ to $122_n$ of FIG. 1, each of the modular recording sites $224_1$ to $224_n$ of FIGS. 2a and 2b and of the modular recording sites $320_1$ to $320_n$ of FIGS. 3a and 3b. The modular recording site 400 comprises a sensor element 410 which can, for example, have the same functionality as each of the sensor elements $322_1$ to $322_n$ of the neuronal probe 300 in FIG. 3a. The sensor element 410 is, for example, coupled to a continuous-time Gm-C Delta-Sigma modulator 420. The time-continuous Gm-C Delta-Sigma modulator 420 can, for example, have the same functionality as the integrator $324_1$ to $324_n$ of FIG. 3a. The continuous-time Gm-C Delta-Sigma modulator 420 can, for example, have a differential input comprising a connection to a sensor element 410 and a connection to a global reference 422. The global reference 422 can, for example, consist of the reference voltage $V_{BODY}$ 333a of the reference 331 in FIG. 3a which represents the reference potential of the brain tissue towards which neural activity is measured. The -continuous-time Gm-C Delta-Sigma modulator is, for example, configured for transferring an output signal to a quantizer 430. The quantizer 430 can, for example, have the same functionality as each quantizer $325_1$ to $325_n$ of FIG. 3a. The quantizer 430 may be coupled to a control unit 440, wherein the control unit 440 can, for example, interact with a control signal 442. The control unit 440 may be coupled to a configuration module 450 and storage 460.

The sensor element 410 of the modular recording site 400 can, for example, receive a neuronal signal and transfer the neuronal signal to the continuous-time Gm-C Delta-Sigma modulator 420. The continuous-time Gm-C Delta-Sigma modulator 420 can then, for example, integrate the neuronal signal and send the integrated neuronal signal to the quantizer 430, wherein the quantizer 430 can, for example, decimate the integrated neuronal signal and convert the neuronal signal into a digital sensor signal. The control unit 440 is, for example, configured to be either in a normal operating mode or in a configuration mode. The control signal 442 may tell the control unit 440 which mode is appropriate. When the control unit operates in the normal operating mode, the digitized sensor signal from the quantizer 430 may be written in the storage 460 and transferred by a digital data bus 462 to a base. When the control unit 440 operates in the configuration mode, the control unit 440 may transmit configuration parameters to the configuration module 450, wherein the configuration module 450 can thereby, for example, change parameters for operating each modular recording site such as, for example, the scaling of the continuous-time Gm-C Delta-Sigma modulator 420 is changed.

In other words, the communication interface (for example, control unit 440 and the storage 460) can, for example, operate either in a configuration mode or in a normal operating mode. The switching between the configuration mode and the normal operating mode can, for example, be carried out by a separate control signal. In the configuration mode, the setting of each modular recording site can, for example, be read out of the received configuration data and be used by each modular recording site for adapting a parameter relating to the operation of the modular recording site 400. In a normal operating mode of the communication interface of each modular recording site of the plurality of modular recording sites, the digital sensor signals can be transferred to the base. With the implementation of the communication interface in each modular recording site it is possible to operate each modular recording site individually and to change parameters regarding the conversion of the neuronal signal into a digital sensor signal.

For example, a digital data bus 462 comprising a storage 460 (the storage 460 is, for example, a transistor) couples the communication interface of each modular recording site of the plurality of modular recording sites serially with respect to each other and to the base. The line for the control signal 442 and the line for the digital data bus 462 do not necessarily have to be individual lines. It is, for example, possible to transmit the control signal 442 using the data bus 462. If the communication interface is in a normal operating mode the digital sensor signal converted by each modular recording site of the plurality of modular recording sites from the neuronal signal can, for example, be written in the storage 460 of the digital data bus 462. The digital data bus 462 then, for example, transfers the storage with the digital sensor signal to the base. The communication interfaces of each modular recording site of the plurality of modular recording sites are connected serially with respect to each other and to the base. This can mean that each communication interface of each modular recording site writes the respective digital sensor signal in the storage 460 of the digital data bus 462, so that the digital sensor signals of each modular recording site are arranged in sequence respective to a position of each modular recording site with respect to a position of each other modular recording site. With a separate control signal, the communication interface can change its mode from a normal operation mode (where the digital sensor signal is transferred from each modular recording site to the base) to configuration mode (where configuration data is transferred from the base to each modular recording site). Thus, this modular system concept allows, for example, the contacting of an arbitrary number of modular recording sites (for example neuronal electrodes of any topology or geometry) with minimum complexity, a small size of the base and reading out the modular recording sites simultaneously.

In other words, the architecture of an analog-to-digital converter (respectively, the modular recording site 400) resembles the architecture of a time-continuous Gm-C Delta-Sigma modulator. The time-continuous Delta-Sigma modulators are known for their reduced demand of electrical power. An implementation with a Gm-C integrator 420 has additionally the advantage that the area demand can be very small. Furthermore, these converters are known that they comprise an implicit anti-aliasing filter effect. Thus, more electrical power and area can be saved, because the necessity for a dedicated anti-aliasing filter as an additionally circuit block can be omitted. The usage of such converters and circuit architecture makes it possible to reduce the signal chain and to put an analog-to-digital converter directly under a sensor element 410.

Figure 4B:
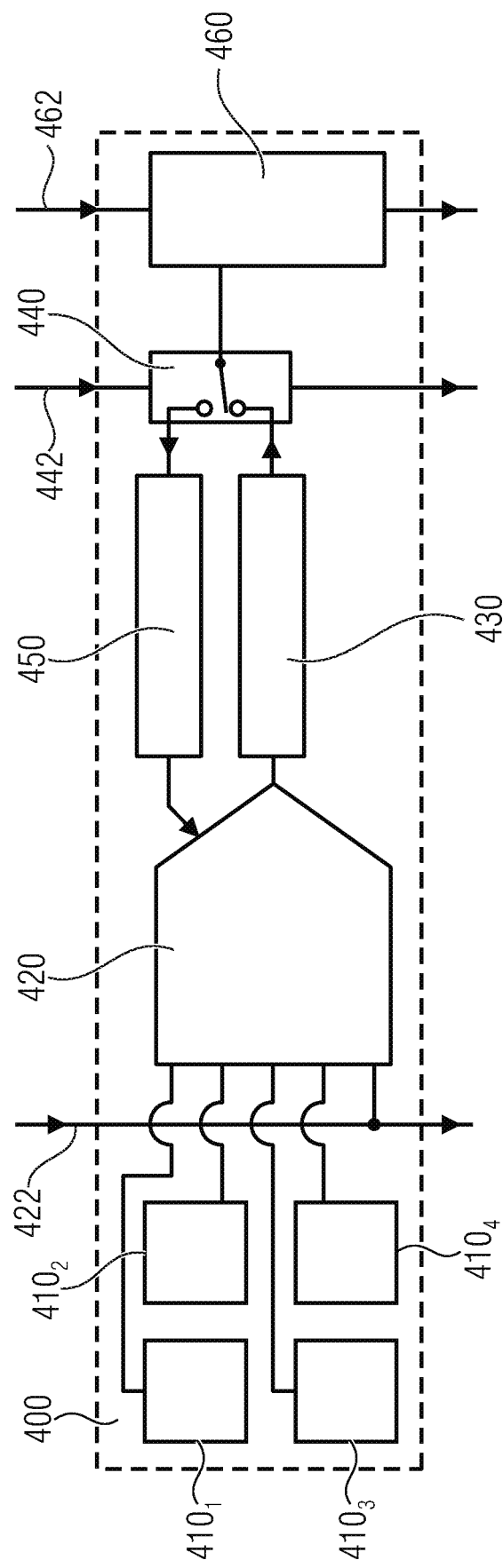
FIG. 4b shows a schematic block diagram of a modular recording site with four sensor elements according to an embodiment of the present invention.

FIG. 4b shows a block diagram of a modular recording site 400, wherein the modular recording site 400 can comprise features and functionalities of the modular recording site 400 shown in FIG. 4a. The modular recording site 400 shown in FIG. 4b differs from the modular recording site 400 in FIG. 4a with regard to the sensor element, wherein the modular recording site 400 of FIG. 4a comprises according to an embodiment at least a second sensor element, by way of example four sensor elements $410_1$ to $410_2$ instead of only one sensor element 410 as in FIG. 4a. The number of four sensor elements is selected for explanatory reasons only and does not limit the scope of the described embodiments. Any other suitable number of two or more, three or more, five or more or even higher numbers such as at least 10 or at least 15 may be implemented. In FIG. 4b equal or equivalent elements or elements with equal or equivalent functionality, compared to elements shown in FIG. 4a, are denoted by equal or equivalent reference numerals even if occurring in different figures. The sensor elements $410_1$ to $410_4$ can also be understood as sensor portions or electrodes.

The at least two sensor elements $410_1$ and $410_2$ are adapted for receiving a signal. The two or more sensor elements $410_1$ to $410_4$ are, for example, arranged in a 2×2-sensor matrix, representing four sensor elements $410_1$ to $410_4$. According to an embodiment all sensor elements $410_1$ to $410_4$ of one modular recording site 400 can detect the same signal, whereby each sensor element $410_1$ to $410_4$ generates for example a different individual signal associated with the same signal, based on a dependency of the same signal on different positions of the sensor elements $410_1$ to $410_4$ at the modular recording site 400. That is, the same signal, the biosignal for example, is received at the different sensor elements $410_1$ to $410_4$ such that the sensor elements $410_1$ to $410_4$ provide for individual, different signal being based on the same biosignal as described in connection with other embodiments of the present invention.

Thus, according to an embodiment, the modular recording site 400 is configured to process four individual signals, associated with the received signal. The individual signals can differ from each other or at least some of the individual signals can be the same. The integrator 420 may integrate the individual signals of the at least to sensor elements $410_1$ and $410_2$ in a time-sequential manner, thereby allowing the modular recording site 400 for sequentially providing an output signal based on two or more sensor elements, i.e., to time-multiplex the information collected with the sensor elements $410_1$ and $410_2$. This may allow for a higher resolution and/or for an oversampling of the signal sensed with the sensor elements $410_1$ and $410_2$ without providing for respective components for conversion of the provided analogue electronic signal into the digital signal.

According to an embodiment FIG. 4b shows an implementation of the modular recording site 400, where one analog-to-digital-converter (e.g. the Gm-C integrator 420 and the quantizer 430) is configured for converting two or more individual provided by the two or more sensor elements $410_1$ to $410_4$. The analog-to-digital-converter is, for example, configured for selectively converting the output of the sensor elements $410_1$ to $410_4$. Time-multiplexing is a widely used method to minimize complexity. According to the described embodiment having a number of sensor elements being four, a four times faster analog-to-digital-converter (when compared to FIG. 4a) can sample and quantize signals received by four sensor elements $410_1$ to $410_4$ in the same time as the analog-to-digital converter described with regard to FIG. 4a converting only one signal, i.e., instead of individually arranging additional converters, a higher conversion speed may be used to group a set of sensor elements.

That is, one, more or all modular recording sites of the probe may be configured for sampling a biosignal with at least a first and a second sensor element and for multiplexing outputs of the first and the second sensor element into the digital sensor signal. Alternatively or in addition to a time-multiplexing, a different or further concept of multiplexing may be implemented, e.g., a frequency-multiplex.

FIG. 5a shows a block diagram of a modular recording site 500 and FIG. 5b shows a circuit diagram of a Gm-C integrator 510 with current feedback, a latched comparator 520 and an output latch 530.

The modular recording site 500 from FIG. 5a comprises a Gm-C integrator 510, wherein the Gm-C integrator 510 has, for example, a differential input comprising a contact to a sensor element 511 (for example, an electrode) and to a reference voltage $V_{BODY}$ 512. The integrator 510 is controlled by a control voltage $V_{BIAS}$ 513 and is connected to a supply voltage $V_{DD}$ 514, wherein a full-scale mode select 516 can be applied. The sensor element 511 can, for example, have the same functionality as each of the sensor elements $322_1$ to $322_n$ of FIG. 3a or FIG. 3b, the reference voltage $V_{BODY}$ 512 can, for example, have the same functionality as the reference voltage 333a of FIG. 3a or FIG. 3b and the supply voltage 514 can, for example, have the same functionality as the supply voltage $V_{DD,A}$ 335 of FIG. 3a or FIG. 3b and the control voltage $V_{BIAS}$ 513 can, for example, have the same functionality as the control voltage 333b of FIG. 3a or FIG. 3b. The integrator 510 has a differential output coupled to a quantizer 620, wherein the quantizer 520 can, for example, have the same functionality as each of the quantizers $325_1$ to $325_n$ of FIG. 3a. From the quantizer 520, a feedback current 528 is coupled to the integrator 510 and a bitstream can be sent to a counter 530, wherein the counter 530 can, for example, have the same functionality as each of the counters $325_1$ to $326_n$ of FIG. 3a.

The quantizer 520 may comprise a reset 522, a clock 524 and a delay clock 526, wherein the delay clock 626 connects to the next side in chain (to the next modular recording site).

The reset 522, for example, switches a transistor to reset the quantizer 520. Thus, for example, by, the quantizer 520 a digitized sensor signal gets delayed in respect to the digital sensor signal of a neighboring modular recording site. The counter 530 is, for example, a ten-bit counter with a reset 532 and a clock 534. The counter 530 writes, for example, the digital sensor signal into a latch 540 (which has, for example, the function of the storage 460 from FIG. 4a and FIG. 4b). The digital sensor signal is then from the latch 540 written into the result register 650, wherein the result register 550 can, for example, have the same functionality as the storage 460 from FIG. 4a and FIG. 4b. Through the input 552, a data chain coming from the base goes into the result register 550 and leaves after receiving an additional digital sensor signal from the latch 540 through the output 554.

In FIG. 5b, the block diagram of FIG. 5a is shown in more detail. The Gm-C integrator is, for example, connected to two global analog lines (the reference voltage $V_{BODY}$ 512 and the control voltage $V_{BIAS}$ 513). The integrator also comprises, for example, the supply voltage $V_{DD}$ 514, wherein the supply voltage 514 creates a current from a first output 514a to a first input 514b and a current from a second output 514c to a second input 514d. The integrator 510 may be connected to a sensor element 511 (for example, an electrode) and can, for example, comprise a reset module 516. The integrator 510 couples, for example, with a latched comparator 570 by a connection between a first differential output 517 to a first differential input 517a and by a second differential output 518 to a second differential input 518a. The latched comparator 570 comprises, for example, a reset 622, a first clock 524a, a second clock 524b, a third clock 524c and a delay clock 528, wherein the first clock 524a, the second clock 524b, the third clock 524c and/or the delay clock 526 operate cyclically and are, for example, provided with the same signal. The latched comparator 570 is connected with an output latch 580 by the supply voltage $V_{DD}$ 514. The output latch 580 is connected to the integrator 510 by a connection between a feedback output 528a and a feedback input 528b.

The feedback current sinks (for example, the connection between the feedback output 528a and the feedback input 528b) are, for example, derived from the global bias line (control voltage 513). The feedback current, for example, determines the full-scale (FS) of the ADC which can be configured to ±11.25 mV, ±22.5 mV or ±45 mV. Depending on the comparator output (for example, the feedback output 528a), the current may be injected either to the left or the right low-impedance cascade node of the OTA (integrator 510). Common mode ripple caused by the asymmetrical feedback may be reduced by connecting the 95 fF MIM integration capacitances (a first MIM (metal/insulator/metal) integration capacitance 519a and a second MIM integration capacitance 519b, wherein the first MIM integration capacitance 519a and the second MIM integration capacitance 519b each occupy, for example, less area than $20 \times 10$ µm$^2$, $15 \times 7$ µm$^2$ or $10 \times 4$ µm$^2$, such as, for example, $7 \times 3.5$ µm$^2$ and can have a capacitance in the scope of 20 fF to 200 fF, 50 fF to 150 fF or 80 fF to 100 fF, such as, for example, 95 fF) to $V_{CMFB}$ 590 and rejected by the differential comparator input. The noise of the feedback current source and the feedback switches, which may operate at digital-level input signals, is negligible compared to the major noise contributors. The constraints on the area and accuracy of the common-mode feedback is not stringent, first because noise is canceled by the differential nature of the circuit, and second, because no exact common mode is needed at the comparator input (for example, a first input 517a and a second input 518a). The trans-conductance of the differential pair may be determined by thermal noise considerations, e.g., to be in the scope of 1 µS to 20 µS, 2 µS to 10 µS or 3 µS to 5 µS, such as, for example, 4.2 µS. A measured maximal SNR may be less than 300 dB, 200 dB or 100 dB, such as, for example, 65.6 dB (FS=±45 mV) and a THD of, for example, less than 5%, 1% or 0.5%, such as, for example, 0.22% at $V_{PP}$=10 mV (FS=±11.25 mV) is obtained for a tail current of 1.5 µA, according to this example.

In other words, the integrator 510 of each modular recording site of the plurality of modular recording sites is configured to receive the neuronal signal and to integrate the neuronal signal, so as to obtain an integrated neuronal signal. The quantizer 520 of each modular recording site of the plurality of modular recording sites comprises a latched comparator 570 and an output latch 580. The latched comparator 570 is configured to receive the integrated neuronal signal and to quantize the integrated neuronal signal. The output latch 580 is configured to drive switches for a feedback current 528 to the integrator 510, based on the comparator output latch 580. Depending on the comparator output latch 580, the current is injected either to the left or to the right low impedance cascade node of the OTA (the OTA together with a capacitance is an example for an integrator).

FIG. 5b shows, for example, an incremental delta-sigma system-level schematic and transistor-level implementation (for example, the feedback current sources of only one full-scale mode are shown: $I_{FBN}$ (from a first output 514a to a first input 514b), $I_{FBP}$ (from a second output 514c to a second input 514d)).

Figure 6A:
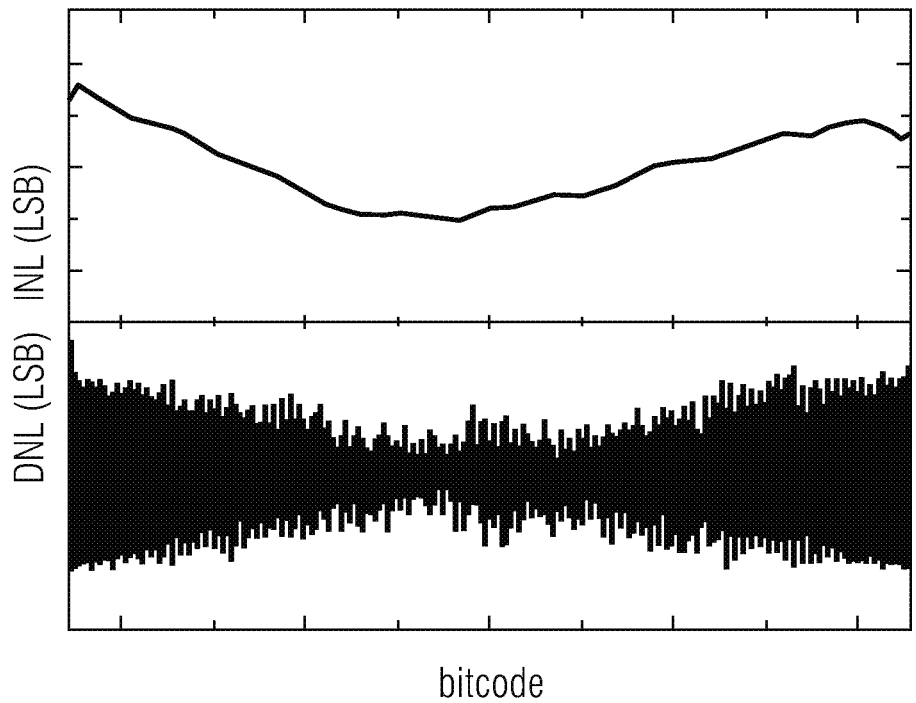
FIG. 6a shows a diagram with measured DNL/INL (differential non-linearity/integral non-linearity) in vitro measurement data measured by a neuronal probe according to an embodiment of the present invention.
Figure 6B:
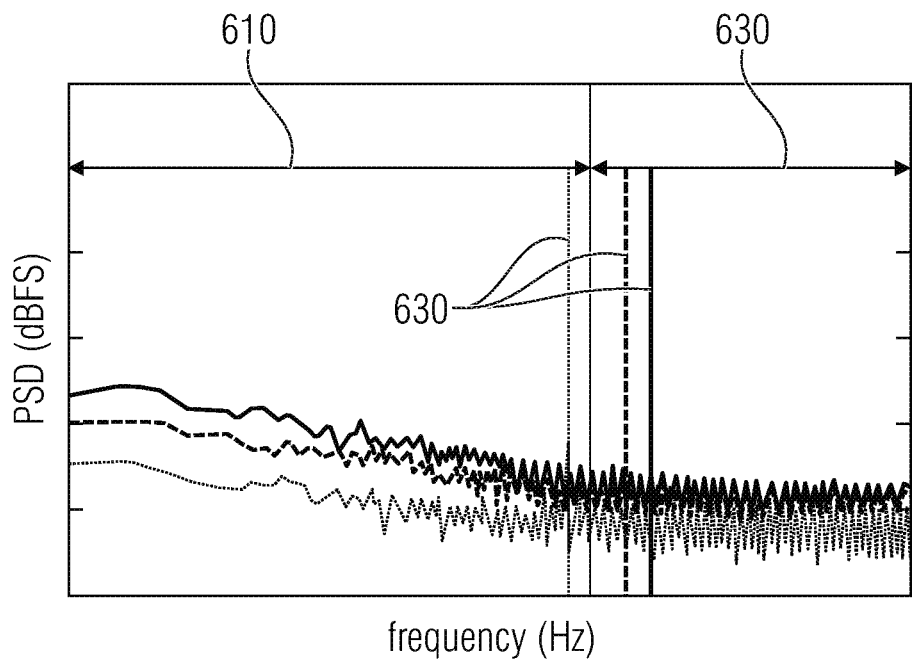
FIG. 6b shows a diagram with an in vitro power spectral density plot measured by a neuronal probe according to an embodiment of the present invention.
Figure 6C:
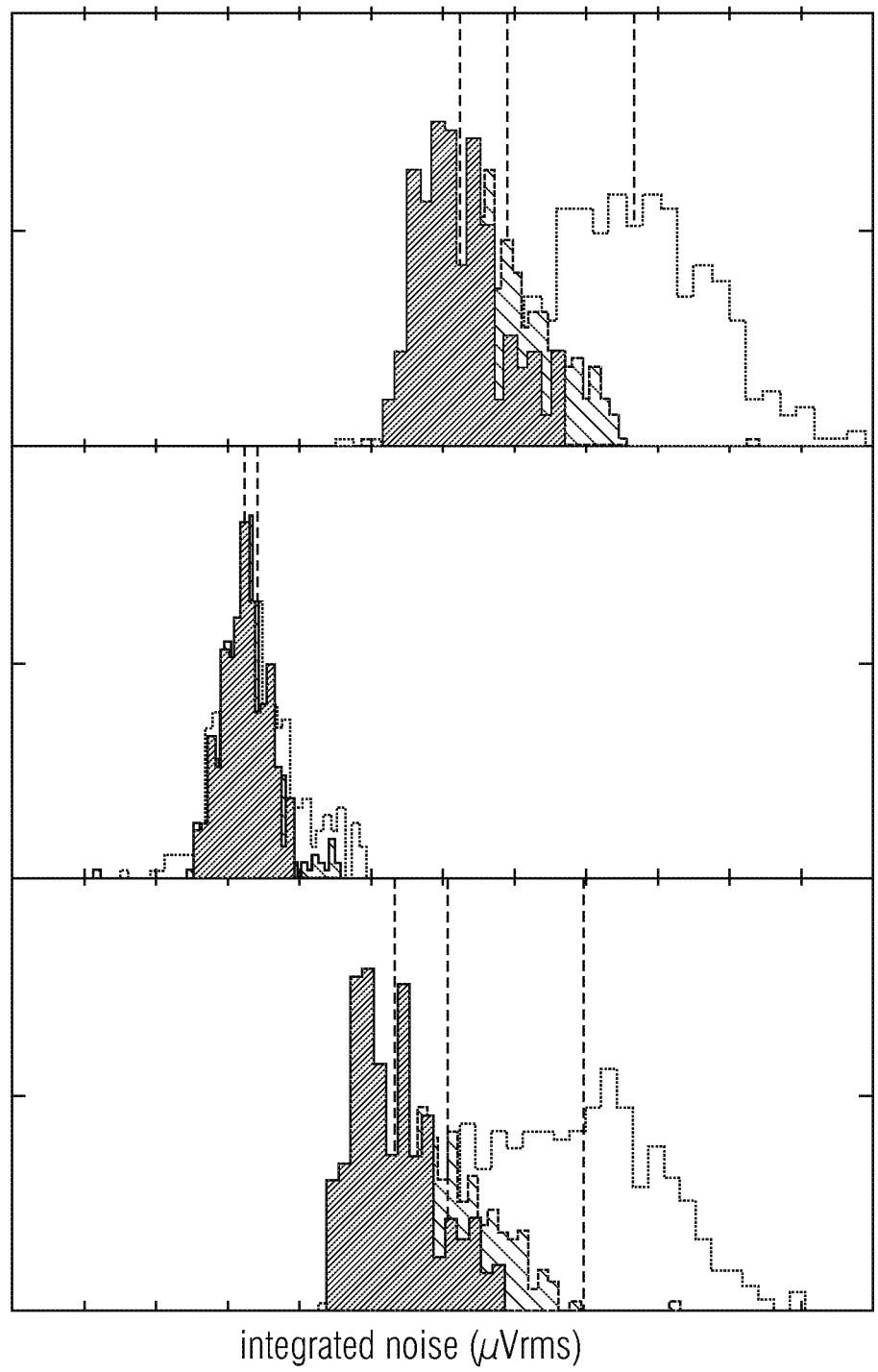
FIG. 6c shows a diagram with a statistical noise distribution of in vitro measurement data measured by a neuronal probe according to an embodiment of the present invention.

FIG. 6a, FIG. 6b and FIG. 6c show diagrams of in vitro measurements, which may be obtained by neuronal probes according to embodiments described herein. Neither the measurement results nor specific details in view of electronic parameters, sizes or numbers given in connection with the embodiments are suitable to limit the teachings given, unless stated otherwise. it is clear that other configurations, parameters, numbers or sizes may be implemented within the scope of the present embodiments.

FIG. 6a shows measured DNL/INL (differential non-linearity/integral non-linearity) for FS=±45 mV. FS means full scale of the ADC (analog-digital converter) which can be configured to ±11.25 mV, ±22.5 mV or ±45 mV.

FIG. 6b shows an in vitro power spectral density plot where the first half 610 corresponds to the LFP band (the band for local-field-potentials) and the second part 620 corresponds to the AP band (action-potential band). FIG. 6b also shows a plurality of noise corners 630.

FIG. 6c shows a statistical noise distribution (384 recording sites—multiple probes). The statistical noise distribution for FS=±11.25 mV is diagrammed in black, for FS=±22.5 mV the statistical noise distribution is shown in light black and for FS=±45 mV the statistical noise distribution is shown in grey. The top most diagram shows the full bandwidth, the middle diagram shows the local field potential band and the lower diagram shows the action potential band. The ADC (analog-digital converter in each modular recording site of a neuronal probe according to an embodiment) covers an input signal bandwidth of 10 kHz with a flicker noise corner between 240 Hz and 590 Hz, depending on the FS mode. The noise in the frequency bands of the two types of neural signals, i.e., local-field-potentials (LFP, 1 to 300 Hz) and action potentials (AP, 0.3 to 10 kHz) are 8.1 µVrms and 13.4 µVrms, respectively (FS=±11.25 mV). All measurements are taken in vitro, i.e., include also noise resulting from the electrodes and the electrolyte surface interface, and without any additional shielding.

Figure 7:
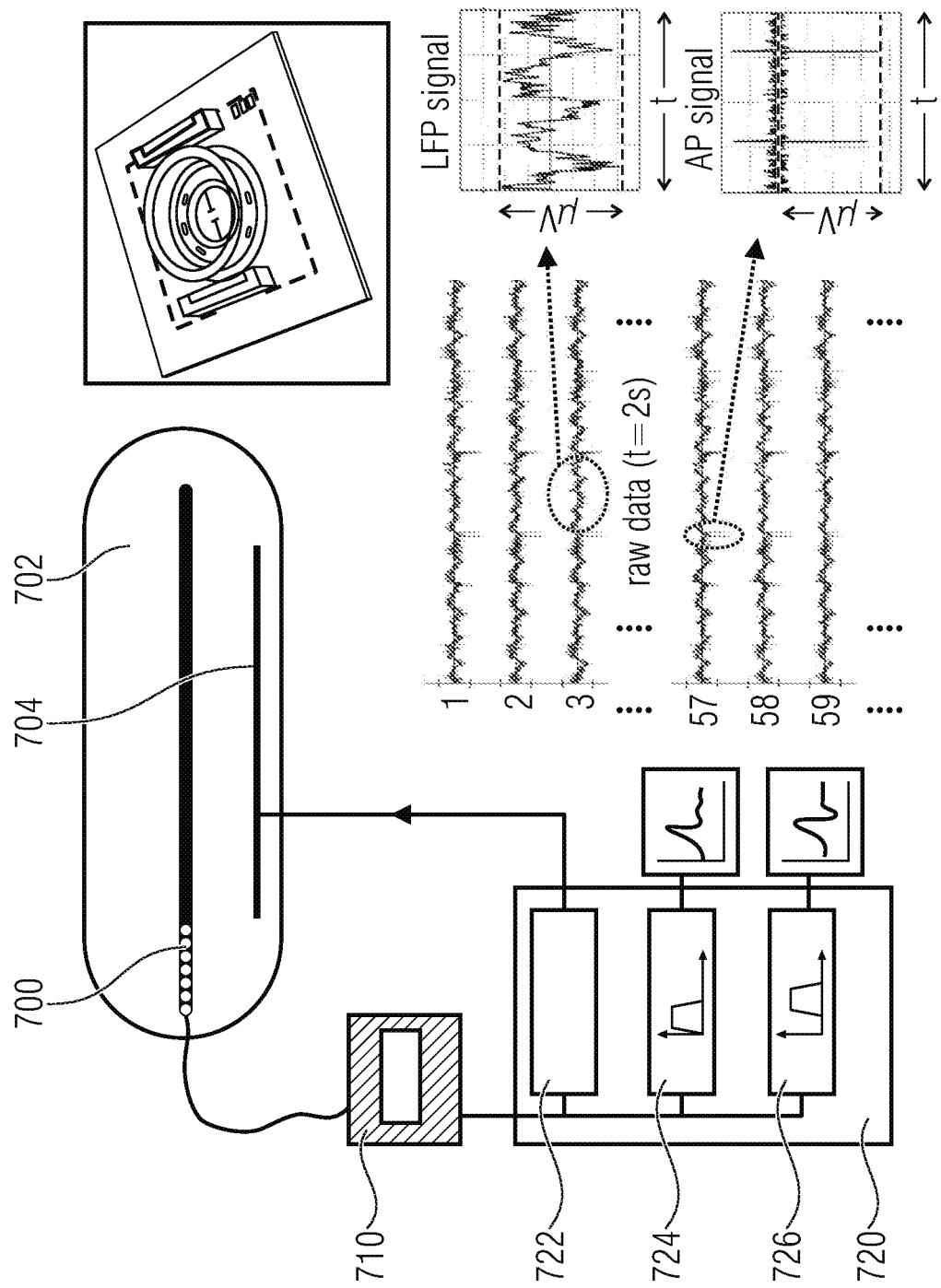
FIG. 7 shows a schematic view of an in vitro measurement setup with a neuronal probe according to an embodiment of the present invention.

FIG. 7 shows an in vitro measurement setup showing DC (direct current) controller/artefact filter and digital post-processing. Measurement results from stimulation with pre-recorded data (hippocampus). The photo on the top right shows in vitro MEA adapter with two needle probes for brain slice activity recording. The neuronal probe 700 (which can, for example, have the same functionalities as the neuronal probe 100, 200 and 300) is put into a phosphate-buffered saline solution 702 with a body voltage $V_{BODY}$ 704. The neuronal probe 700 is connected via a flex-cable to a field-programmable-gate-array 710 (FPGA). The FPGA 710 is connected via USB (universal serial bus) to a post-processing unit 720. The post-processing unit 720 comprises a DC controller artefact filter 722, a LFP filter 724 and an AP filter 726.

In the following, an example measurement is described shortly. The averaged data of all ADCs (analog-digital converter in each modular recording site of a neuronal probe according to an embodiment) is used to drive a proper body voltage for the application in saline solution and for cancellation of artifact signals. The measured signal is separated into low frequency local-field potentials (LFP) and high-frequency action potentials (AP) by digital post-processing.

Figure 8:
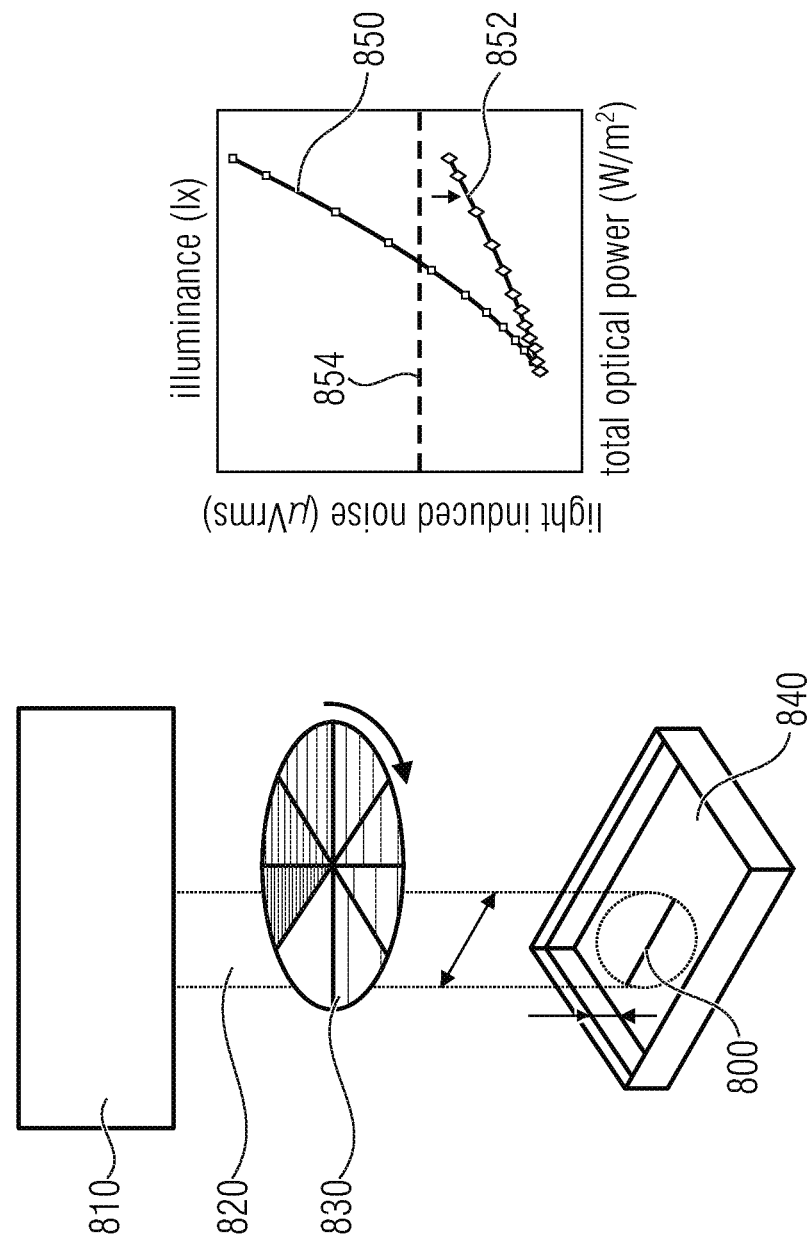
FIG. 8 shows photometric and radiometric light sensitivity measurements for optogenetic applications with a neuronal probe according to an embodiment of the present invention.

FIG. 8 shows a photometric and radiometric light sensitivity measurement (average noise of all illuminated recording sites) for optogenetic applications (for comparison: an illuminance of about 500 Lux corresponds to typical office lighting, about 10000 Lux to full daylight). During optogenetic stimulation an external light source excites specifically brain tissue and therefore, activity can be elicited, which can be detected with the neuronal probe. Generally light pulses also generate in neuronal probes artefact signals. The design of the neuronal probe, as described herein, is implemented such to be to a large extend immune to optical disruptions.

A pulsing (on/off with a frequency of 20 Hz or 1 kHz) broadband light source 810 ($\lambda$=400 nm to 1000 nm) may sends a beam 820 through a neutral density filter 830 onto an active needle probe 800 (the active needle probe 800 can, for example, have the same functionality as the neuronal probe 100, 200 and 300), wherein the active needle probe 800 is placed in a ringer solution 840. In the right diagram the first curve 850 corresponds to a high frequency (for example, 1 kHz) and a second curve 852 corresponds to a low frequency (for example, 20 Hz). In the diagram is also shown the full bandwidth noise limit 854. The shielding and layout concept (as described above) of the neuronal probe according to an embodiment with both input transistors of a differential pair (The differential transistor pair, describes a circuit technique in which two input transistors are used in order to create differential signaling in the signal path.) placed under the electrode suppresses illumination artifacts, which is a strong requirement for optogenetic stimulation of neuronal cells [9]. Sensitivity measurements against pulsing broadband light sources are shown in FIG. 8. The resulting signal shifts during light excitation are consistent with photonic effects on the electrode surface while the CMOS circuit underneath does not further degrade the performance.

Figure 9:
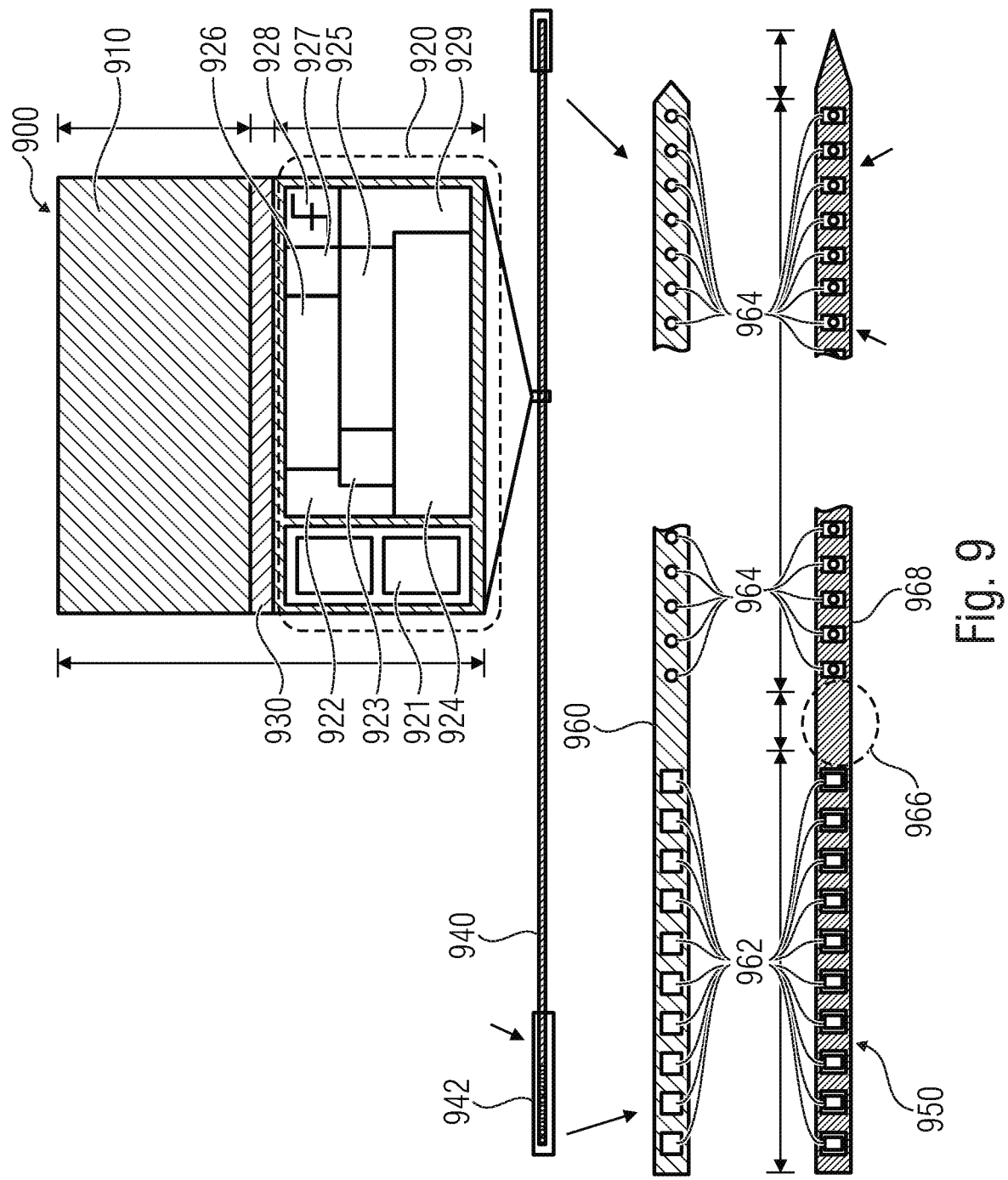
FIG. 9 shows micrographs of a CMOS chip and a neuronal probe according to an embodiment of the present invention.

FIG. 9 shows micrographs showing CMOS chip and final needle probe (an example for a neuronal probe according to an embodiment) after post-CMOS processing (supply voltages are tight together off-chip) on the cable. The pad is, for example, used for electrode characterization (for example, cyclic voltammetry or electrochemical impedance spectroscopy), it is not necessarily needed for the read out. One modular recording site 900 of a neuronal probe according to the present invention can be separated in a digital part 910 and an analog part 920 separated by a shield 930. The analog part 920 comprises, for example, a Gm integrator 921, a CMFB 922 (a C 923, a CMOS load 924, switches 925, current bias 926, $V_B$ 927, a quantizer 928 and a configuration module 929).

The neuronal probe 940 comprises an optional first electrode 942, wherein the first electrode (for example, a Pt-electrode) can be directly connected to $V_{REF}$ pad for electrode characterization. The neuronal probe 960 comprises Pads 962 and sensor elements 964, wherein the Pads 962 are, for example a contacting to connect the neuronal probe 960 to external device. The neuronal probe 950 comprises Pads 962, sensor elements 964, a base 966 and an optional $Si_3N_4$—$SiO_2$ passivation, wherein the Pads 962 are, for example a contacting to connect the neuronal probe 960 to an external device, the sensor elements 964 are, for example, Pt-electrodes (platinum-electrodes) and the $Si_3N_4$—$SiO_2$ passivation forms an insulating portion 968 between each sensor element 964. The neuronal probe is separated after post-CMOS fabrication.

The micrographs show the fully implantable probe with, for example, a constant width of 70 µm and thickness of 50 µm from tip to base. The length of the base is, for example, independent on the number of electrodes. The maximal number of recording sites may be solely limited by the data rate of the chain as the clock frequency equals to fs of the ADCs. Each ADC delivers, for example, 20 kS/s, limiting the length to, for example, 93 electrodes per chain. An example probe employs, for example, two data chains (each with, for example, 93 modular recording sites); however, an extension with multiple chains would only add marginal complexity to the digital part. Since no global analog neural signal routing may be present and due to the high modularity of the design, a longer probe or any application-specific modification of the probe geometry would deliver identical performance. Technology scaling would considerably reduce the power dissipation as well as the probe width, since half the probe area is dedicated to the digital circuitry.

FIG. 10*a* shows a schematic view of a neuronal probe 1000 as stated in the art, FIG. 10*b* shows a neuronal probe 1100 according to an embodiment of the present invention. All known solutions have a very large base 1010 and hence cannot completely be buried in the tissue. Additionally, the size of the base 1010 involves an invasive surgical procedure. With the neuronal probe 1100, these problems can be overcome. Accordingly, it can be seen that the neuronal probe according to the present invention clearly outperforms conventional solutions.

FIG. 11 shows a neuronal probe according to the state of the art with a base 1110, a shaft 1120 and a signal processing unit 1130. The signal processing unit 1130 comprises a signal amplifier 1132, an analog-to-digital conversion 1134, a digital processing/interface 1136 and a computer 1138.

With the neuronal probe as described herein a number of components of the signal processing unit 1130 can be reduced by omitting the signal amplifier 1132 and the analog/digital conversion 1134. For example the neuronal probe already includes those components in each modular recording side. Accordingly, it can be seen that the neuronal probe according to the present invention clearly outperforms conventional solutions.

Figure 12:
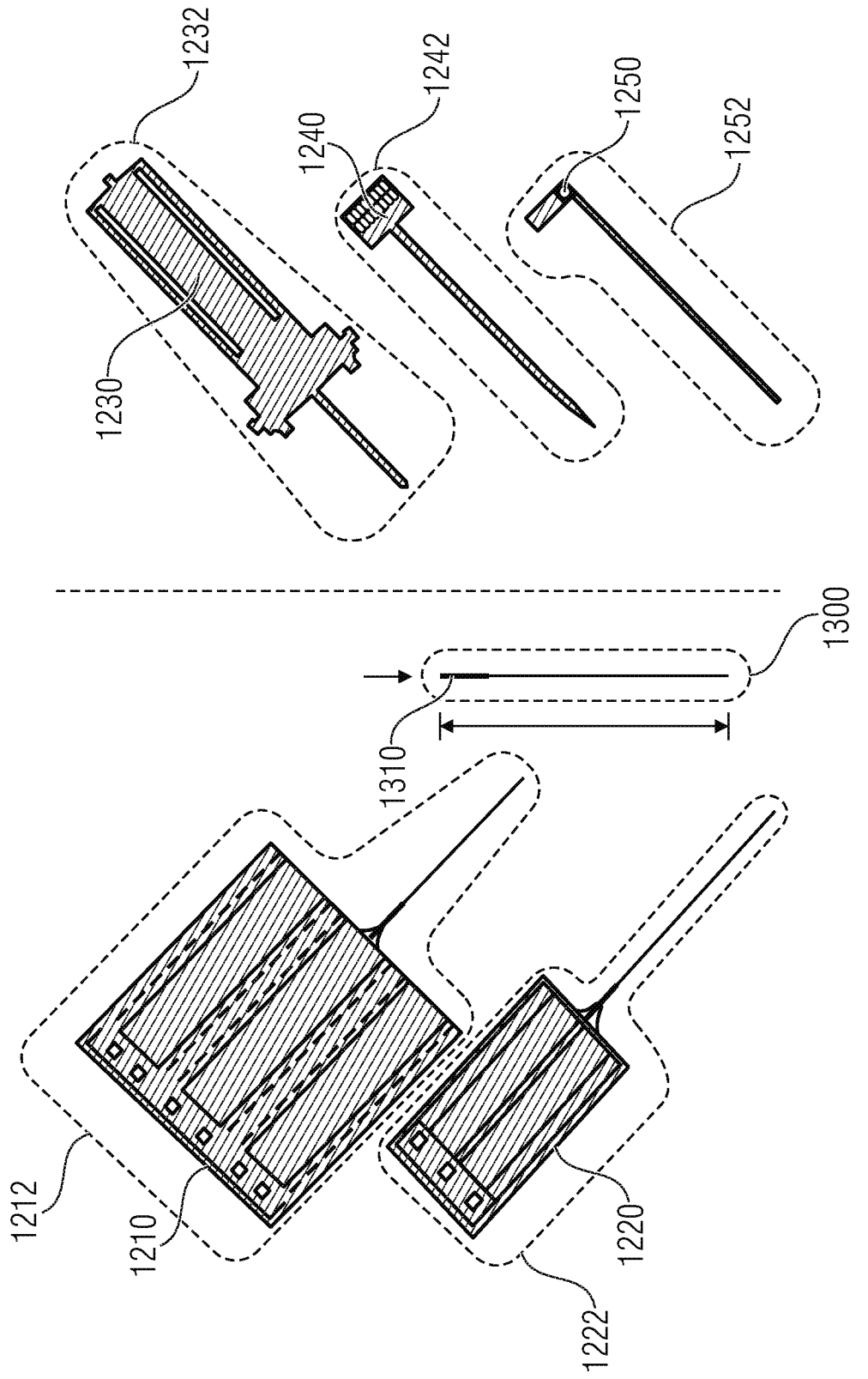
FIG. 12 shows a comparison of different neuronal probes including a neuronal probe according to an embodiment of the present invention.

FIG. 12 shows neuronal probes as stated in the art (neuronal probe 1212, 1222, 1232, 1242 and 1252) in comparison with a neuronal probe 1300 (an embodiment of the present Invention), as presented in this application. It can be seen, that the neuronal probe 1300 as described herein comprises a very small base 1310. The base 1310 may be implemented much smaller than the base 1210, 1220, 1230, 1240 and 1250. Thus the neuronal probe 1300 can be buried in tissue much easier and deeper than with the neuronal probes 1212, 1222, 1232, 1242 and 1252. Accordingly, it can be seen that the neuronal probe according to the present invention clearly outperforms conventional solutions.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus like, for example, a microprocessor, a programmable computer or an electronic circuit. In some embodiments, one or more of the most important method steps may be executed by such an apparatus.

Depending on certain implementation requirements, embodiments of the invention can be implemented in hardware or in software. The implementation can be performed using a digital storage medium, for example, a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitionary.

A further embodiment of the inventive method is, therefore, a data stream or a sequence of signals representing the computer program for performing one of the methods described herein. The data stream or the sequence of signals may, for example, be configured to be transferred via a data communication connection, for example, via the Internet.

A further embodiment comprises a processing means, for example, a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are performed by any hardware apparatus.

The apparatus described herein may be implemented using a hardware apparatus, or using a computer, or using a combination of a hardware apparatus and a computer.

The apparatus described herein, or any components of the apparatus described herein, may be implemented at least partially in hardware and/or in software.

The methods described herein may be performed using a hardware apparatus, or using a computer, or using a combination of a hardware apparatus and a computer.

The methods described herein, or any components of the apparatus described herein, may be performed at least partially by hardware and/or by software.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

REFERENCES

[1] G. Buzsaki et al., "Tools for Probing Local Circuits: High-Density Silicon Probes Combined with Optogenetics," Neuron, vol. 88, pp. 92-105, 2015.

[2] K. Seidl, M. Schwaerzle, I. Ulbert, H. P. Neves, O. Paul and P. Ruttier, "CMOS-Based High-Density Silicon Microprobe Arrays for Electronic Depth Control in Intracortical Neural Recording-Characterization and Application," in Journal of Microelectromechanical Systems, vol. 21, no. 6, pp. 1428-1435, December 2012.

[3] A. S. Herbawi et al., "High-density CMOS neural probe implementing a hierarchical addressing scheme for 1600 recording sites and 32 output channels," Transducers, pp. 20-23, 2017.

[4] V. Viswam at al., "High-density mapping of brain slices using a large multi-functional high-density CMOS microelectrode array system," Transducers, pp. 135-138. 2017, doi: 10.1109/TRANSDUCERS.2017.7994006

[5] B. C. Raducanu et al., "Time multiplexed active neural probe with 678 parallel recording sites", IEEE ESS-DERC, 2016, pp. 385-388.

[6] C. M. Lopez et al., "22.7 A 966-electrode neural probe with 384 configurable channels in 0.13 μm SOI CMOS," ISSCC Dig, Tech. Papers, pp. 392-393, 2016, pp. 392-393, 2016.

[7] F Heer, W Franks, A Blau, S Taschini, C Ziegler, A Hierlemann, H Baltes, CMOS mioroelectrode array for the monitoring of electrogenic cells, Biosensors and Bioelectronics, vol. 20. pp. 358-366, 2004, ISSN 0956-5663. doi: 10.1016/j.bios.2004.02.006.

[8] J. Sohoivin at al., "Close-packed silicon microelectrodes for scalable spatially oversampled neural recording", EEE Trans. Biomed. Eng., vol. 63, pp. 120-130, 2016.

[9] T. D. Y. Kozel and A. L. Vazquez, "Photoelectric Artefact from Optogenetics and Imaging on Microelectrodes and Bioelectronics: New Challenges and Opportunities," J. Mater. Chem. 6, pp. 4965-4978, 2015.

The invention claimed is:

1. A sensor array comprising:
   a base for providing a probe signal forming a proximal side of the sensor array;
   a plurality of modular recording sites in communication with the base and arranged at a distal side of the sensor array, wherein each modular recording site of the plurality of modular recording sites comprises,
   a CMOS complementary metal-oxide-semiconductor) silicon substrate,
   at least one sensor element configured for receiving an analog biosignal,
   an analog-to-digital converter disposed on the CMOS silicon substrate and configured for converting the analog biosignal into a digital sensor signal and
   a communication interface configured to provide the digital sensor signal to the base;
   wherein the communication interfaces of the plurality of modular recording sites are connected serially with respect to each other and to the base.

2. The sensor array according to claim 1, wherein the base is configured for receiving a plurality of digital sensor signals from the plurality of modular recording sites and to process the plurality of digital sensor signals so as to provide the probe signal.

3. The sensor array according to claim 1, wherein the communication interface of each modular recording site of the plurality of modular recording sites is configured to receive configuration data from the base, wherein the modular recording site is configured for adapting a parameter relating to the operation of the modular recording site based on the received configuration data.

4. The sensor array according to claim 1, wherein each communication interface of the plurality of modular recording sites comprises a serial interface,
   wherein the communication interfaces of the plurality of modular recording sites are connected to each other in a serial communication chain comprising a forward path from the base to a sensor array endpoint of the sensor array and a backward path from the sensor array endpoint to the base, wherein for each pair of a first modular recording site and a neighboring second modular recording site, the communication interface of the first modular recording site is connected to the forward path and the communication interface of the second modular recording site is connected to the backward path.

5. The sensor array according to claim 1, wherein the base is configured to receive a combined sensor signal from the plurality of modular recording sites, the combined sensor signal comprising the digital sensor signals of each of the modular recording sites.

6. The sensor array according to claim 1, wherein each analog-to-digital converter comprises a delta-sigma-analog-digital converter.

7. The sensor array according to claim 1, wherein each analog-to-digital converter comprises an integrator and a quantizer configured to convert directly the analog biosignal into the digital sensor signal.

8. The sensor array according to claim 1, wherein each modular recording site of the plurality of modular recording sites is configured for converting the analog biosignal into the digital sensor signal independently of neighboring modular recording sites.

9. The sensor array according to claim 1, wherein the plurality of modular recording sites is arranged along an axial direction and forms an array along the axial direction; wherein an extension of the base along a first perpendicular direction perpendicular to the axial direction is at most an extension of the plurality of modular recording sites along the first perpendicular direction; and wherein an extension of the base along a second perpendicular direction perpendicular to the axial direction is at most an extension of the plurality of modular recording sites along the second perpendicular direction.

10. The sensor array according to claim 1, wherein a cross section of the plurality of modular recording sites in a plane perpendicular to an axial extension of the sensor array is independent of the number of modular recording sites.

11. The sensor array according to claim 1, wherein the sensor array comprises one column comprising the plurality of modular recording sites; or comprising a plurality of columns each comprising a plurality of plurality of modular recording sites having a communication interface, the communication interfaces of the plurality of modular recording sites connected serially with respect to each other.

12. The sensor array according to claim 1, wherein a first subset of the plurality of modular recording sites is arranged on a first semiconductor substrate, and wherein an adjacent and neighboring second subset of the plurality of modular recording sites is arranged on a second semiconductor substrate; wherein the first semiconductor substrate and the second semiconductor substrate are spaced apart from each other by a gap and electrically connected to each other by at least one conductive line.

13. The sensor array according to claim 1, wherein the at least one conductive line is arranged on or in a flexible substrate.

14. The sensor array according to claim 1, wherein the base comprises a wired output interface for providing the probe signal, wherein a number of channels of the wired output interface is independent of the number of modular recording sites and independent of a cross section of the plurality of modular recording sites in a plane perpendicular to an axial extension of the sensor array.

15. The sensor array according to claim 1, wherein the plurality of modular recording sites is arranged between the base and a sensor array endpoint of the sensor array, wherein the sensor array forms a needle.

16. The sensor array according to claim 1, wherein a modular recording site of the plurality of modular recording sites comprises a housing, the housing comprising a sensor portion for receiving the analog biosignal and comprising an insulating portion for insulating the sensor portion from a sensor portion of the housing of an adjacent modular recording site.

17. The sensor array according to claim 1, wherein a modular recording site of the plurality of modular recording sites comprises a housing, the housing comprising two or more sensor portions for receiving the analog biosignal and comprising an insulating portion for insulating each sensor portion from another sensor portion of the two or more sensor portions.

18. The sensor array according to claim 1, wherein at least one modular recording site of the sensor array is configured for sampling the analog biosignal with at least a first and a second sensor element and for multiplexing outputs of the first and the second sensor element into the digital sensor signal.

19. The sensor array according to claim 1, wherein each modular recording site of the plurality of modular recording sites is divided into an analog part and a digital part,
wherein the analog part and the digital part comprise a separate supply routing,
wherein the digital part is shielded from the analog part by a first conductive element,
wherein a second conductive element is arranged encircling a connector of the sensor element so as to shield the analog part and the digital part from the sensor element,
wherein the analog part is configured to convert the analog biosignal received by the sensor element into the digital sensor signal,
wherein the analog part and the digital part are coupled for providing the digital sensor signal to the digital part,
wherein the digital part is configured to provide the digital sensor signal to the base.

20. The sensor array according to claim 1, wherein the sensor array is a biomedical sensor array, in particular a neuronal probe.

21. A method for operating the sensor array according to claim 1, comprising:
recording of an analog biosignal with the sensor element of a modular recording site of the plurality of modular recording sites of the sensor array;
converting of the analog biosignal into a plurality of digital sensor signals using the analog-to-digital-converters of the plurality of modular recording sites of the sensor array;
providing of the plurality of digital sensor signals to the base of the sensor array using the communication interfaces of the plurality of modular recording sites of the sensor array;
providing the digital sensor signal to the base using the communication interface of the modular recording site, serially by using the communication interfaces of the plurality of modular recording sites;
receiving of the plurality of digital sensor signals from the plurality of modular recording sites of the sensor array with the base of the sensor array;
processing of the plurality of digital sensor signals by the base of the sensor array so as to acquire the probe signal; and
providing the probe signal with the base of the sensor array for a remote device.

22. A non-transitory digital storage medium having a computer program stored thereon to perform the method for operating the sensor array according to claim 1, comprising:
recording of an analog biosignal with the sensor element of a modular recording site of the plurality of modular recording sites of the sensor array;
converting of the analog biosignal into a plurality of digital sensor signals using the analog-to-digital-converters of the plurality of modular recording sites of the sensor array;
providing of the plurality of digital sensor signals to the base of the sensor array using the communication interfaces of the plurality of modular recording sites of the sensor array;
providing the digital sensor signal to the base using the communication interface of the modular recording site, serially by using the communication interfaces of the plurality of modular recording sites;
receiving of the plurality of digital sensor signals from the plurality of modular recording sites of the sensor array with the base of the sensor array;

processing of the plurality of digital sensor signals by the base of the sensor array so as to acquire the probe signal; and providing the probe signal with the base of the sensor array for a remote device, when said computer program is run by a computer.

* * * * *

UNITED STATES PATENT AND TRADEMARK OFFICE
CERTIFICATE OF CORRECTION

| | | |
|---|---|---|
| PATENT NO. | : 11,986,304 B2 | Page 1 of 1 |
| APPLICATION NO. | : 16/986322 | |
| DATED | : May 21, 2024 | |
| INVENTOR(S) | : Yiannos Manoli et al. | |

It is certified that error appears in the above-identified patent and that said Letters Patent is hereby corrected as shown below:

On the Title Page

Item (72) (inventors), for the last named inventor please delete "Oslo (DE)" and insert therefor --Oslo (NO)--

Signed and Sealed this
Twenty-fifth Day of June, 2024

Katherine Kelly Vidal
*Director of the United States Patent and Trademark Office*